(12) United States Patent
Szyf et al.

(10) Patent No.: US 7,465,714 B2
(45) Date of Patent: Dec. 16, 2008

(54) OLIGONUCLEOTIDE INHIBITORS OF MBD2/DNA DEMETHYLASE AND USES THEREOF

(75) Inventors: Moshe Szyf, Cote St. Luc (CA); Paul Campbell, Oshawa (CA)

(73) Assignee: McGill University, Montreal, Quebec (CA)

( * ) Notice: Subject to any disclaimer, the term of this patent is extended or adjusted under 35 U.S.C. 154(b) by 108 days.

(21) Appl. No.: 10/518,470

(22) PCT Filed: Jun. 20, 2003

(86) PCT No.: PCT/CA03/00884

§ 371 (c)(1),
(2), (4) Date: Nov. 14, 2005

(87) PCT Pub. No.: WO04/001027

PCT Pub. Date: Dec. 31, 2003

(65) Prior Publication Data

US 2006/0166909 A1     Jul. 27, 2006

(51) Int. Cl.
| | |
|---|---|
| A01N 43/04 | (2006.01) |
| A61K 31/70 | (2006.01) |
| C07H 21/02 | (2006.01) |
| C07H 21/04 | (2006.01) |
| C12N 5/00 | (2006.01) |
| C12N 5/06 | (2006.01) |
| C12Q 1/68 | (2006.01) |

(52) U.S. Cl. ............. 514/44; 536/23.1; 536/24.5; 435/325; 435/333
(58) Field of Classification Search ........... 536/24.5; 514/44; 435/6, 320.1
See application file for complete search history.

(56) References Cited

U.S. PATENT DOCUMENTS 5,877,009 A * 3/1999 Zannis et al. ............ 435/320.1
5,877,309 A * 3/1999 McKay et al. ............. 536/24.5
6,905,827 B2 * 6/2005 Wohlgemuth et al. ......... 435/6
2006/0009403 A1 * 1/2006 Bigey et al. ................ 514/44

OTHER PUBLICATIONS

Slack et al., Antisense MBD2 gene therapy inhibits tumorigenesis, Published online May 17, 2002, The Journal of Gene Medicine, vol. 4, pp. 381-389.*
Merriam-Webster Online Dictionary, "Definition of prevent", p. 1 of 2 is enclosed.*
Opalinska et al., Nucleic-acid therapeutics: Basic principles and recent applications, Jul. 2002, Nature Reviews Drug Discovery, vol. 1, pp. 503-514.*
Charlie Schmidt, Negotiating the RNAi patent thicket, Mar. 2007, Nature Biotechnology, vol. 25, pp. 273-275.*
Walton et al., Antisense Technology, 2000, The Biomedical Engineering Handbook, Second Edition, Chapter 103, CRC Press LLC.*
Marsh et al., Genetic insights into familial cancers—update and recent discoveries, 2002, Cancer Letters, vol. 181, pp. 125-164.*
Merriam-Webster Online Dictionary, "Definition of prevent", p. 1 of 2 is enclosed "http://m-w.com/dictionary/prevent" accessed on Jun. 4, 2007.*
Elbashir et al., RNA interference is mediated by 21- and 22-nucleotide RNAs, 2001, Genes & Development, vol. 15, pp. 188-200.*

* cited by examiner

Primary Examiner—J. E. Angell
Assistant Examiner—Dana Shin
(74) Attorney, Agent, or Firm—France Cote Bereskin and Parr

(57) ABSTRACT

Oligonucleotide inhibitors that inhibit expression of a mammalian MBD2/DNA demethylase (MBD2/dMTase) are provided. The oligonucleotide inhibitors can be used to inhibit the growth or proliferation of tumor cells in vitro and in vivo. The use of the oligonucleotide inhibitors in the treatment of cancer and methods of identifying potential target genes for cancer therapy or diagnosis using the oligonucleotide inhibitors are also provided.

12 Claims, 17 Drawing Sheets

FIGURE 1

```
              v10       v20       v30       v40       v50       v60       v70       v80       v90       v100      v110
MRAHPGGGRCCPEQEEGESAAGGSGAGGDSAIEQGGQGSALAPSPVSGVRREGARGGGRGRGRGRWKQAGRGGVCGRGRGRGRGRGRGRGRGRGRGRPPSGGSGLGGDGGG
MRAHPGGGRCCPEQEEGESAAGGSGAGGDSAIEQGGQGSALAPSPVSGVRREGARGGGRGRGRGRWKQA:RGGGVCGRGRGRGRGRGRGRGRGRGRGRP.SGGSGLGGDGGG
MRAHPGGGRCCPEQEEGESAAGGSGAGGDSAIEQGGQGSALAPSPVSGVRREGARGGGRGRGRGRWKQAARGGGVCGRGRGRGRGRGRGRGRGRGRGRPQSGGSGLGGDGGG
              ^10       ^20       ^30       ^40       ^50       ^60       ^70       ^80       ^90       ^100      ^110
              v120      v130      v140      v150      v160      v170      v180      v190      v200      v210
CG3G---GSGGGGAPRREPVFPSGSAGPGPRGPRATESGKRMDCPALPPGWKKEEVIRKSGLSAGKSDVYYFSPSGKKFRSKPQLARYLGNTVDLSSFDFRTGKMMPSK
:GG    GSGGG APRR:PVFPSGS:GPGPRGPRATESGKRMDCPALPPGWKKEEVIRKSGLSAGKSDVYYFSPSGKKFRSKPQLARYLGN:VDLSSFDFRTGKMMPSK
GASGCGVGSGGGVAPRRDPVFPSGSSGPGPRGPRATESGKRMDCPALPPGWKKEEVIRKSGLSAGKSDVYYFSPSGKKFRSKPQLARYLGNAVDLSSFDFRTGKMMPSK
              ^120      ^130      ^140      ^150      ^160      ^170      ^180      ^190      ^200      ^210      ^220
              v220      v230      v240      v250      v260      v270      v280      v290      v300      v310      v320
LQKNKQRLRNDPLNQNKGKPDLNTTLPIRQTASIEKQPVTKVTNHPSNKVKSDPQRMNEQPRQLFWEKRLQGLSASDVTEQIIKTMELPKGLQGVGPGSNDETLLSAVAS
LQKNKQRLRNDPLNQNKGKPDLNTTLPIRQTASIEKQPVTK TNHPSNKVKSDPQRMNEQPRQLFWEKRLQGLSASDVTEQIIKTMELPKGLQGVGPGSNDETLLSAVAS
LQKNKQRLRNDPLNQNKGKPDLNTTLPIRQTASIEKQPVTKFTNHPSNKVKSDPQRMNEQPRQLFWEKRLQGLSASDVTEQIIKTMELPKGLQGVGPGSNDETLLSAVAS
              ^230      ^240      ^250      ^260      ^270      ^280      ^290      ^300      ^310      ^320
              v330      v340      v350      v360      v370      v380      v390      v400      v410
ALHTSSAPITGQVSAAVEKNPAVWLNTSQPLCKAFIVTDEDIRKQEERVQQVRKKLEEALMADILSRAADTEEMDIEMDSGDEA
ALHTSSAPITGQVSAAVEKNPAVWLNTSQPLCKAFIVTDEDIRKQEERVQQVRKKLEEALMADILSRAADTEE:DI:MDSGDEA
ALHTSSAPITGQVSAAVEKNPAVWLNTSQPLCKAFIVTDEDIRKQEERVQQVRKKLEEALMADILSRAADTEEVDIDMDSGDEA
              ^340      ^350      ^360      ^370      ^380      ^390      ^400      ^410
```

FIGURE 2

SEQUENCE LISTING

<160> NUMBER OF SEQ ID NOS: 15

<210> SEQ ID NO 1
<211> LENGTH: 2584
<212> TYPE: DNA
<213> ORGANISM: Homo sapiens
<220> FEATURE:
<221> NAME/KEY: misc_feature
<222> LOCATION: (0)...(0)
<223> OTHER INFORMATION: cDNA MBD2/dMTase

<400> SEQUENCE: 1

```
gggggcgtgg ccccgagaag gcggagacaa gatggccgcc catagcgctt ggaggaccta      60
agaggcggtg gccggggcca cgccccgggc aggagggccg ctctgtgcgc gcccgctcta     120
tgatgcttgc gcgcgtcccc cgcgcgccgc gctgcgggcg gggcgggtct ccgggattcc     180
aagggctcgg ttacggaaga agcgcagcgc cggctgggga ggggctgga tgcgcgcgca      240
cccgggggga ggccgctgct gcccggagca ggaggagggg gagagtgcgg cgggcggcag     300
cggcgctggc ggcgactccg ccatagagca gggggggccag ggcagcgcgc tcgccccgtc    360
cccggtgagc ggcgtgcgca gggaaggcgc tcggggcggc ggccgtggcc ggggcggtg      420
gaagcaggcg ggccggggcg gcggcgtctg tggccgtggc cggggccggg gccgtggccg     480
gggacgggga cggggccggg gccggggccg cggccgtccc ccgagtggcg gcagcggcct     540
tggcggcgac ggcggcggct gcggcggcgg cggcagcggt ggcggcggcg ccccccggcg     600
ggagccggtc cctttcccgt cggggagcgc ggggccgggg cccaggggac cccgggccac     660
ggagagcggg aagaggatgg attgcccggc cctcccccc ggatggaaga aggaggaagt      720
gatccgaaaa tctgggctaa gtgctggcaa gagcgatgtc tactacttca gtccaagtgg     780
taagaagttc agaagcaagc ctcagttggc aaggtacctg ggaaatactg ttgatctcag     840
cagttttgac ttcagaactg gaaagatgat gcctagtaaa ttacagaaga acaaacagag     900
actgcgaaac gatcctctca atcaaaataa gggtaaacca gacttgaata caacattgcc     960
aattagacaa acagcatcaa ttttcaaaca accggtaacc aaagtcacaa atcatcctag    1020
taataaagtg aaatcagacc cacaacgaat gaatgaacag ccacgtcagc tttttctggga   1080
gaagaggcta caaggactta gtgcatcaga tgtaacagaa caaattataa aaaccatgga    1140
actacccaaa ggtcttcaag gagttggtcc aggtagcaat gatgagaccc ttttatctgc    1200
tgttgccagt gctttgcaca caagctctgc gccaatcaca gggcaagtct ccgctgctgt    1260
ggaaaagaac cctgctgttt ggcttaacac atctcaaccc ctctgcaaag cttttattgt    1320
cacagatgaa gacatcagga acaggaaga gcgagtacag caagtacgca agaaattgga    1380
agaagcactg atggcagaca tcttgtcgcg agctgctgat acagaagaga tggatattga    1440
aatggacagt ggagatgaag cctaagaata tgatcaggta actttcgacc gactttcccc    1500
aagagaaaat tcctagaaat tgaacaaaaa tgtttccact ggcttttgcc tgtaagaaaa    1560
aaaatgtacc cgagcacata gagcttttta atagcactaa ccaatgcctt tttagatgta    1620
tttttgatgt atatatctat tattcaaaaa atcatgttta ttttgagtcc taggacttaa    1680
aattagtctt ttgtaatatc aagcaggacc ctaagatgaa gctgagcttt tgatgccagg    1740
```

-continued

```
tgcaatctac tggaaatgta gcacttacgt aaaacatttg tttcccccac agttttaata    1800
agaacagatc aggaattcta ataaaatttc ccagttaaag attattgtga cttcactgta    1860
tataaacata ttttatact ttattgaaag gggacacctg tacattcttc catcatcact    1920
gtaaagacaa ataaatgatt atattcacag actgattgga attctttctg ttgaaaagca    1980
cacacaataa agaacccctc gttagccttc ctctgattta cattcaactc tgatccctgg    2040
gccttaggtt tgacatggag gtggaggaag atagcgcata tatttgcagt atgaactatt    2100
gcctctggac gttgtgagaa ttgtgctttc accagaattt ctaagaattt ctgctaaata    2160
tcacctagca tgtgtaattt ttttttccttg cctgtgactt ggactttttga tagttctata    2220
agaataaggc ttttttcttcc cttgggcatg agtcagatac acaaggaccc ttcaggtgtt    2280
actagaaggc gtccatgttt attgtttttt aaagaatgtt tggcactctc taacgtccac    2340
tagcttactg agttatcagg tgcaggtcag actcttggct acagtgagag cagcttcta    2400
ggcagagttg cttaatgaaa gggtttgtaa tactttacaa accattacct gtacctggcc    2460
tggcctccaa aatattaaca ttcttttttct gttgaaactc gcgagtgtaa ctttcatacc    2520
acttgaattt attgatattt aattatgaaa actagcatta cattattaaa cgatttctaa    2580
aatc                                                                 2584
```

<210> SEQ ID NO 2
<211> LENGTH: 411
<212> TYPE: PRT
<213> ORGANISM: Homo sapiens

<400> SEQUENCE: 2

```
Met Arg Ala His Pro Gly Gly Gly Arg Cys Cys Pro Glu Gln Glu Glu
  1               5                  10                  15

Gly Glu Ser Ala Ala Gly Gly Ser Gly Ala Gly Gly Asp Ser Ala Ile
             20                  25                  30

Glu Gln Gly Gly Gln Gly Ser Ala Leu Ala Pro Ser Pro Val Ser Gly
         35                  40                  45

Val Arg Arg Glu Gly Ala Arg Gly Gly Arg Gly Arg Gly Arg Trp
     50                  55                  60

Lys Gln Ala Gly Arg Gly Gly Val Cys Gly Arg Gly Arg
 65                  70                  75                  80

Gly Arg Gly Arg Gly Arg Gly Arg Gly Arg Gly Arg Gly Arg
                 85                  90                  95

Pro Pro Ser Gly Ser Gly Leu Gly Gly Asp Gly Gly Cys Gly
            100                 105                 110

Gly Gly Gly Ser Gly Gly Gly Ala Pro Arg Arg Glu Pro Val Pro
            115                 120                 125

Phe Pro Ser Gly Ser Ala Gly Pro Gly Pro Arg Gly Pro Arg Ala Thr
        130                 135                 140

Glu Ser Gly Lys Arg Met Asp Cys Pro Ala Leu Pro Pro Gly Trp Lys
145                 150                 155                 160

Lys Glu Glu Val Ile Arg Lys Ser Gly Leu Ser Ala Gly Lys Ser Asp
                165                 170                 175

Val Tyr Tyr Phe Ser Pro Ser Gly Lys Lys Phe Arg Ser Lys Pro Gln
            180                 185                 190

Leu Ala Arg Tyr Leu Gly Asn Thr Val Asp Leu Ser Ser Phe Asp Phe
        195                 200                 205

Arg Thr Gly Lys Met Met Pro Ser Lys Leu Gln Lys Asn Lys Gln Arg
    210                 215                 220
```

-continued

```
Leu Arg Asn Asp Pro Leu Asn Gln Asn Lys Gly Lys Pro Asp Leu Asn
225                 230                 235                 240

Thr Thr Leu Pro Ile Arg Gln Thr Ala Ser Ile Phe Lys Gln Pro Val
            245                 250                 255

Thr Lys Val Thr Asn His Pro Ser Asn Lys Val Lys Ser Asp Pro Gln
            260                 265                 270

Arg Met Asn Glu Gln Pro Arg Gln Leu Phe Trp Glu Lys Arg Leu Gln
            275                 280                 285

Gly Leu Ser Ala Ser Asp Val Thr Glu Gln Ile Ile Lys Thr Met Glu
            290                 295                 300

Leu Pro Lys Gly Leu Gln Gly Val Gly Pro Gly Ser Asn Asp Glu Thr
305                 310                 315                 320

Leu Leu Ser Ala Val Ala Ser Ala Leu His Thr Ser Ser Ala Pro Ile
                325                 330                 335

Thr Gly Gln Val Ser Ala Ala Val Glu Lys Asn Pro Ala Val Trp Leu
                340                 345                 350

Asn Thr Ser Gln Pro Leu Cys Lys Ala Phe Ile Val Thr Asp Glu Asp
            355                 360                 365

Ile Arg Lys Gln Glu Glu Arg Val Gln Gln Val Arg Lys Lys Leu Glu
            370                 375                 380

Glu Ala Leu Met Ala Asp Ile Leu Ser Arg Ala Ala Asp Thr Glu Glu
385                 390                 395                 400

Met Asp Ile Glu Met Asp Ser Gly Asp Glu Ala
                405                 410

<210> SEQ ID NO 3
<211> LENGTH: 1953
<212> TYPE: DNA
<213> ORGANISM: Mus musculus
<220> FEATURE:
<221> NAME/KEY: misc_feature
<222> LOCATION: (0)...(0)
<223> OTHER INFORMATION: cDNA MBD2/dMTase

<400> SEQUENCE: 3 gggggcgtg  gcccagagga  ggcggagaca  atatggcctc  gcccctagct  tggaggacct    60
aagaggcgcg  gccggggcca  cgccccgggc  gggaggggccg  ctctgtgcgc  gcccgctcta   120
tgatgcttgc  gcgcgtcccc  cgcgcgccgc  tctgcgggcg  gggcgggtct  ccgggattcc   180
aagggctcgg  ttacggaaga  agcgcagagc  cggctgggga  gggggctgga  tgcgcgcgca   240
cccgggggga  ggccgctgct  gcccggagca  ggaggagggg  gagagcgcgg  cgggcggcag   300
cggcgctggc  ggcgactccg  ccatagagca  gggggggccag  ggcagcgcgc  tcgctccgtc   360
cccggtgagc  ggcgtgcgca  gggaaggcgc  tcggggcggc  ggccgtggcc  gggggcggtg   420
gaagcaggcg  gcccggggcg  gcggcgtctg  tggccgtggc  cgtggccgtg  gccgggtcg   480 gggccgtggc  cggggccggg  gccggggccg  cggccgtccc  cagagtggcg  gcagcggcct   540
tggcggcgac  ggcggcggcg  gcgcgggcgg  ctgcggcgtc  ggcagcggtg  gcggcgtcgc   600 ccccggcgg  gatcctgtcc  ctttcccgtc  ggggagctcg  gggccggggc  caggggacc   660 ccgggccacg  gagagcggga  agaggatgga  ctgcccggcc  ctcccccccg  gatgaagaa   720 ggaggaagtg  atccgaaaat  cagggctcag  tgctggcaag  agcgatgtct  actacttcag   780
tccaagtggt  aagaagttca  gaagtaaacc  tcagctggca  agatacctgg  gaaatgctgt   840
tgaccttagc  agttttgact  tcaggaccgg  caagatgatg  cctagtaaat  tacagaagaa   900
```

-continued

```
caagcagaga ctccggaatg acccccctcaa tcagaacaag ggtaaaccag acctgaacac    960
aacattgcca attagacaaa ctgcatcaat tttcaagcaa ccagtaacca aattcacgaa   1020
ccacccgagc aataaggtga agtcagaccc ccagcggatg aatgaacaac acgtcagct    1080
tttctgggag aagaggctac aaggacttag cgcatcagat gtaacagaac aaattataaa   1140
aaccatggag ctacctaaag gtcttcaagg agtcggtcca ggtagcaatg acgagaccct   1200
tctgtctgct gtggccagtg ctttacacac aagctctgcg cccatcacag acaagtctc    1260
tgctgccgtg gaaagaaacc ctgctgtttg gcttaacaca tctcaacccc tctgcaaagc   1320
tttcattgtt acagatgaag acattaggaa acaggaagag cgagtccaac aagtacgcaa   1380
gaaactggag gaggcactga tggccgacat cctgtcccgg gctgcggaca cggaggaagt   1440
agacattgac atggacagtg gagatgaggc gtaagaatat gatcaggtaa ctttcgactg   1500
accttcccca agagcaaatt gctagaaaca gaattaaaac atttccactg ggtttcgcct   1560
gtaagaaaaa gtgtacctga gcacatagct ttttaatagc actaaccaat gccttttag    1620
atgtattttt gatgtatata tctattattc caaatgatgt ttattttgaa tcctaggact   1680
taaaatgagt cttttataat agcaagcagg gcccttccgg tgcagtgcag ctttgaggcc   1740
aggtgcagtc tactggaaag gtagcactta cgtgaaatat ttgtttcccc cacagtttta   1800
atataaacag atcaggagta ccaaataagt ttcccaatta aagattatta tacttcactg   1860
tatataaaca gatttttata ctttattgaa agaagatacc tgtacattct tccatcatca   1920
ctgtaaagac aaataaatga ctatattcac aga                                1953
```

<210> SEQ ID NO 4
<211> LENGTH: 414
<212> TYPE: PRT
<213> ORGANISM: Mus musculus

<400> SEQUENCE: 4

```
Met Arg Ala His Pro Gly Gly Gly Arg Cys Cys Pro Glu Gln Glu Glu
  1               5                  10                  15
Gly Glu Ser Ala Ala Gly Gly Ser Gly Ala Gly Gly Asp Ser Ala Ile
             20                  25                  30
Glu Gln Gly Gly Gln Gly Ser Ala Leu Ala Pro Ser Pro Val Ser Gly
         35                  40                  45
Val Arg Arg Glu Gly Ala Arg Gly Gly Arg Gly Arg Gly Arg Gly Trp
     50                  55                  60
Lys Gln Ala Ala Arg Gly Gly Gly Val Cys Gly Arg Gly Arg Gly Arg
 65                  70                  75                  80
Gly Arg Gly Arg Gly Arg Gly Arg Gly Arg Gly Arg Gly Arg Gly Arg
                 85                  90                  95
Pro Gln Ser Gly Gly Ser Gly Leu Gly Gly Asp Gly Gly Gly Gly Ala
                100                 105                 110
Gly Gly Cys Gly Val Gly Ser Gly Gly Val Ala Pro Arg Arg Asp
            115                 120                 125
Pro Val Pro Phe Pro Ser Gly Ser Ser Gly Pro Gly Pro Arg Gly Pro
        130                 135                 140
Arg Ala Thr Glu Ser Gly Lys Arg Met Asp Cys Pro Ala Leu Pro Pro
145                 150                 155                 160
Gly Trp Lys Lys Glu Glu Val Ile Arg Lys Ser Gly Leu Ser Ala Gly
                165                 170                 175
Lys Ser Asp Val Tyr Tyr Phe Ser Pro Ser Gly Lys Lys Phe Arg Ser
            180                 185                 190
```

```
Lys Pro Gln Leu Ala Arg Tyr Leu Gly Asn Ala Val Asp Leu Ser Ser
            195                 200                 205

Phe Asp Phe Arg Thr Gly Lys Met Met Pro Ser Lys Leu Gln Lys Asn
        210                 215                 220

Lys Gln Arg Leu Arg Asn Asp Pro Leu Asn Gln Asn Lys Gly Lys Pro
225                 230                 235                 240

Asp Leu Asn Thr Thr Leu Pro Ile Arg Gln Thr Ala Ser Ile Phe Lys
                245                 250                 255

Gln Pro Val Thr Lys Phe Thr Asn His Pro Ser Asn Lys Val Lys Ser
            260                 265                 270

Asp Pro Gln Arg Met Asn Glu Gln Pro Arg Gln Leu Phe Trp Glu Lys
        275                 280                 285

Arg Leu Gln Gly Leu Ser Ala Ser Asp Val Thr Glu Gln Ile Ile Lys
290                 295                 300

Thr Met Glu Leu Pro Lys Gly Leu Gln Gly Val Gly Pro Gly Ser Asn
305                 310                 315                 320

Asp Glu Thr Leu Leu Ser Ala Val Ala Ser Ala Leu His Thr Ser Ser
                325                 330                 335

Ala Pro Ile Thr Gly Gln Val Ser Ala Ala Val Glu Lys Asn Pro Ala
            340                 345                 350

Val Trp Leu Asn Thr Ser Gln Pro Leu Cys Lys Ala Phe Ile Val Thr
        355                 360                 365

Asp Glu Asp Ile Arg Lys Gln Glu Glu Arg Val Gln Gln Val Arg Lys
370                 375                 380

Lys Leu Glu Glu Ala Leu Met Ala Asp Ile Leu Ser Arg Ala Ala Asp
385                 390                 395                 400

Thr Glu Glu Val Asp Ile Asp Met Asp Ser Gly Asp Glu Ala
                405                 410

<210> SEQ ID NO 5
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 5
ggcaatccat cctcttcc                                                 18

<210> SEQ ID NO 6
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 6
cttcctcctt cttccatc                                                 18

<210> SEQ ID NO 7
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 7
caacagtatt tcccagg                                                  17
```

<210> SEQ ID NO 8
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 8
tgtagcctct tctccca                                                  17

<210> SEQ ID NO 9
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 9
atccagcccc ctccccag                                                 18

<210> SEQ ID NO 10
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 10
cactctcccc ctccccct                                                 18

<210> SEQ ID NO 11
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 11
tcaacagtat ttcccaggta                                               20

<210> SEQ ID NO 12
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 12
ucaacagtat ttcccaggua                                               20

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
auggaccctt tatgacaacu                                               20

<210> SEQ ID NO 14
<211> LENGTH: 20
<212> TYPE: DNA
<213> ORGANISM: Artificial Sequence
<220> FEATURE:
<223> OTHER INFORMATION: oligonucleotide

<400> SEQUENCE: 14
cgattcaatc ctcacctctc                                                   20

<210> SEQ ID NO 15
<211> LENGTH: 2792
<212> TYPE: DNA
<213> ORGANISM: Homo sapiens
<220> FEATURE:
<221> NAME/KEY: misc_feature
<222> LOCATION: (0)...(0)
<223> OTHER INFORMATION: cDNA MBD2/dMTase

<400> SEQUENCE: 15

| | | | | | |
|---|---|---|---|---|---|
| gggggcgtgg | ccccgagaag | gcggagacaa | gatggccgcc | catagcgctt | ggaggaccta | 60 |
| agaggcggtg | gccggggcca | cgccccgggc | aggagggccg | ctctgtgcgc | gcccgctcta | 120 |
| tgatgcttgc | gcgcgtcccc | cgcgcgccgc | gctgcgggcg | gggcgggtct | ccgggattcc | 180 |
| aagggctcgg | ttacggaaga | agcgcagcgc | cggctgggga | ggggctgga | tgcgcgcgca | 240 |
| cccgggggga | ggccgctgct | gcccggagca | ggaggagggg | gagagtgcgg | cgggcggcag | 300 |
| cggcgctggc | ggcgactccg | ccatagagca | gggggggccag | ggcagcgcgc | tcgccccgtc | 360 |
| cccggtgagc | ggcgtgcgca | gggaaggcgc | tcggggcggc | ggccgtggcc | ggggcggtg | 420 |
| gaagcaggcg | ggccggggcg | gcggcgtctg | tggccgtggc | cggggccggg | gccgtggccg | 480 |
| gggacgggga | cggggccggg | gccggggccg | cggccgtccc | ccgagtggcg | gcagcggcct | 540 |
| tggcggcgac | ggcggcggct | gcggcggcgg | cggcagcggt | ggcggcggcg | cccccggcg | 600 |
| ggagccggtc | cctttcccgt | cggggagcgc | ggggccgggg | cccagggac | cccgggccac | 660 |
| ggagagcggg | aagaggatgg | attgcccggc | cctcccccc | ggatggaaga | aggaggaagt | 720 |
| gatccgaaaa | tctgggctaa | gtgctggcaa | gagcgatgtc | tactacttca | gtccaagtgg | 780 |
| taagaagttc | agaagcaagc | tcagttggc | aaggtacctg | ggaaatactg | ttgatctcag | 840 |
| cagttttgac | ttcagaactg | gaaagatgat | gcctagtaaa | ttacagaaga | acaaacagag | 900 |
| actgcgaaac | gatcctctca | atcaaaataa | gctgcgctgg | aacactcatc | gtcctgcacc | 960 |
| atggcatgcg | ctttcaagac | tctgcttgct | catacgctgt | ttgctctgct | tggaatgtgc | 1020 |
| ttacccccctt | ccccttcatc | tggtgaactc | ctactcatcc | aagacccagc | ttcattgtct | 1080 |
| ccatctctgg | gaagcctgcc | ctgcatactc | caggcagaac | caatcctttc | ctccataagg | 1140 |
| gtaaaccaga | cttgaataca | acattgccaa | ttagacaaac | agcatcaatt | ttcaaacaac | 1200 |
| cggtaaccaa | agtcacaaat | catcctagta | ataaagtgaa | atcagaccca | caacgaatga | 1260 |
| atgaacagcc | acgtcagctt | ttctgggaga | agaggctaca | aggacttagt | gcatcagatg | 1320 |
| taacagaaca | aattataaaa | accatggaac | tacccaaagg | tcttcaagga | gttggtccag | 1380 |
| gtagcaatga | tgagaccctt | ttatctgctg | ttgccagtgc | tttgcacaca | agctctgcgc | 1440 |
| caatcacagg | gcaagtctcc | gctgctgtgg | aaaagaaccc | tgctgtttgg | cttaacacat | 1500 |
| ctcaacccct | ctgcaaagct | tttattgtca | cagatgaaga | catcaggaaa | caggaagagc | 1560 |
| gagtacagca | agtacgcaag | aaattggaag | aagcactgat | ggcagacatc | ttgtcgcgag | 1620 |
| ctgctgatac | agaagagatg | gatattgaaa | tggacagtgg | agatgaagcc | taagaatatg | 1680 |
| atcaggtaac | tttcgaccga | cttttcccca | gagaaaattc | ctagaaattg | aacaaaaatg | 1740 |
| tttccactgg | cttttgcctg | taagaaaaaa | aatgtacccg | agcacataga | gcttttttaat | 1800 |
| agcactaacc | aatgccttttt | tagatgtatt | tttgatgtat | atatctatta | ttcaaaaaat | 1860 |

```
catgtttatt ttgagtccta ggacttaaaa ttagtctttt gtaatatcaa gcaggaccct    1920
aagatgaagc tgagcttttg atgccaggtg caatctactg gaaatgtagc acttacgtaa    1980
aacatttgtt tcccccacag ttttaataag aacagatcag gaattctaaa taaatttccc    2040
agttaaagat tattgtgact tcactgtata taaacatatt tttatacttt attgaaaggg    2100
gacacctgta cattcttcca tcatcactgt aaagacaaat aaatgattat attcacagac    2160
tgattggaat tctttctgtt gaaaagcaca cacaataaag aacccctcgt tagccttcct    2220
ctgatttaca ttcaactctg atccctgggc cttaggtttg acatggaggt ggaggaagat    2280
agcgcatata tttgcagtat gaactattgc ctctggacgt tgtgagaatt gtgctttcac    2340
cagaatttct aagaatttct gctaaatatc acctagcatg tgtaattttt tttccttgcc    2400
tgtgacttgg acttttgata gttctataag aataaggctt tttcttccct tgggcatgag    2460
tcagatacac aaggacccett caggtgttac tagaaggcgt ccatgtttat tgttttttaa    2520
agaatgtttg gcactctcta acgtccacta gcttactgag ttatcaggtg caggtcagac    2580
tcttggctac agtgagaggc agcttctagg cagagttgct taatgaaagg gtttgtaata    2640
ctttacaaac cattacctgt acctggcctg gcctccaaaa tattaacatt cttttctgt    2700 tgaaactcgc gagtgtaact ttcataccac ttgaatttat tgatatttaa ttatgaaaac    2760
tagcattaca ttattaaacg atttctaaaa tc                                  2792
```

OLIGONUCLEOTIDE INHIBITORS OF MBD2/DNA DEMETHYLASE AND USES THEREOF

FIELD OF THE INVENTION

The present invention pertains to the fields of cancer therapy and in particular, to oligonucleotide inhibitors of MBD2/dMTase and their use in the treatment of cancer.

BACKGROUND

The epigenome is the physiological template of the genetic information in all eukaryotic cells [Jenuwein, T. and Allis, C. D. (2001) *Science* 293:1074-1080]. The epigenome formats the genetic information by either presenting an accessible structure that can be expressed or by forming an inaccessible structure that cannot be accessed and thus is silenced. The epigenome comprises two major components: a group of proteins called histones that package the DNA into either accessible or inaccessible formats called chromatin, and a coating of methyl groups that are covalently bound to the DNA molecule itself. A long line of data has established that aberrations of the epigenome are a hallmark of all tumour cells, with one of the clear aberrations being global hypomethylation of DNA [Szyf, M. (1996) *Pharmacol Ther* 70:1-37].

DNA methylation is catalysed by the enzyme DNA methyltransferase and occurs via transfer of methyl groups from S-adenosyl methionine to the 5' position of cytosine residues [Adams, R. L. et al. (1984) *Curr Top Microbiol Immunol* 108:142-156]. This process was previously believed to be irreversible, however, a protein exhibiting demethylase activity has recently been identified. The cDNA encoding this methylated DNA binding protein has been cloned and purified [Bhattacharya, S. K. et al. (1999) *Nature* 397:579-583], and the encoded DNA demethylase, also referred to as MBD2, has been shown to exhibit an activity that can reverse the DNA methylation reaction and hence act as a bona fide demethylase [Ramchandani, S. et al. (1999) *Proc Natl Acad Sci USA* 96:6107-6112; Scanlan, M. J. et al. (1998) *Int J Cancer* 76:652-658]. A possible role for DNA demethylase in cancer has been suggested. For example, a nonbiased screen for highly enriched antigens in humans with colorectal cancer uncovered a cDNA identical to that encoding the demethylase protein [Vilain, A. et al. (1999) *FEBS Lett* 460:231-234]. In addition, a recent study of demethylase mRNA expression in various breast cancer cell lines demonstrated a correlation between the level of genome hypomethylation, aberrant chromosomes and expression of the cDNA encoding demethylase [Hattori, M. et al. (2001) *J Int Med Res* 29:204-213]. Similarly, a correlation between malignancy, expression of MBD2/demethylase and demethylation in ovarian cancer has been demonstrated [Hattori, M. et al. (2001) *Cancer Lett* 169:155-164; Kanai, Y. et al. (1999) *Biochem Biophys Res Commun* 264:962-966].

Expression of a reverse-oriented full-length mbd2/dMTase cDNA in human embryonic kidney (HEK) cells has been shown to inhibit anchorage-independent growth of these cells in vitro [International Patent Application No. WO 99/24583]. However, such a large expression construct has limited use in vivo due to such factors as rapid degradation of the expressed transcript by nucleases and poor bioavailability.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide small oligonucleotide MBD2/dMTase inhibitors. In accordance with one aspect of the present invention, there is provided an oligonucleotide inhibitor, or an analogue thereof, comprising from about 7 to about 100 nucleotides complementary to a mammalian MBD2/demethylase mRNA, wherein said oligonucleotide inhibitor, or analogue thereof, inhibits expression of a mammalian MBD2/demethylase gene.

In accordance with another aspect of the present invention, there is provided an oligonucleotide inhibitor, or an analogue thereof, of less than about 100 nucleotides in length comprising at least 7 consecutive nucleotides from the sequence as set forth in any one of SEQ ID NOs: 5, 6, 7, 8, 9, 10, 11 or 12.

In accordance with another aspect of the present invention, there is provided a vector comprising an oligonucleotide inhibitor of MBD2/dMTase.

In accordance with another aspect of the present invention, there is provided a host cell comprising an oligonucleotide inhibitor of MBD2/dMTase, or comprising a vector comprising the oligonucleotide inhibitor.

In accordance with a further aspect of the present invention, there is provided a pharmaceutical composition comprising an oligonucleotide inhibitor of MBD2/dMTase, or comprising a vector comprising the oligonucleotide inhibitor.

In accordance with still another aspect of the present invention, there is provided a use of an oligonucleotide inhibitor of MBD2/dMTase, or a vector comprising the oligonucleotide inhibitor, in the manufacture of a medicament.

In accordance with still another aspect of the present invention, there is provided a use of an oligonucleotide inhibitor, or an analogue thereof, comprising from about 7 to about 100 nucleotides complementary to a mammalian MBD2/demethylase mRNA, to inhibit the growth of cancer cells in a mammal in need thereof.

In accordance with still another aspect of the present invention, there is provided a use of an oligonucleotide inhibitor, or an analogue thereof, comprising from about 7 to about 100 nucleotides complementary to a mammalian MBD2/demethylase mRNA, to inhibit the proliferation of cancer cells in a mammal in need thereof.

In accordance with still another aspect of the present invention, there is provided a use of an oligonucleotide inhibitor, or an analogue thereof, comprising from about 7 to about 100 nucleotides complementary to a mammalian MBD2/demethylase mRNA, in the treatment of cancer in a mammal.

In accordance with still another aspect of the present invention, there is provided a use of an oligonucleotide inhibitor, or an analogue thereof, comprising from about 7 to about 100 nucleotides complementary to a mammalian MBD2/demethylase mRNA, in the prophylactic treatment of a mammal to prevent a familial cancer.

In accordance with still another aspect of the present invention, there is provided a method of identifying target genes for cancer therapy comprising treating a cell with one or more oligonucleotide inhibitor of a mammalian MBD2/demethylase gene, analysing gene expression in the treated cell and comparing the gene expression with gene expression in a control cell not treated with said oligonucleotide inhibitor, wherein a difference in gene expression between the treated cell and the control cell is indicative of one or more target gene.

BRIEF DESCRIPTION OF THE FIGURES

Figure 1:
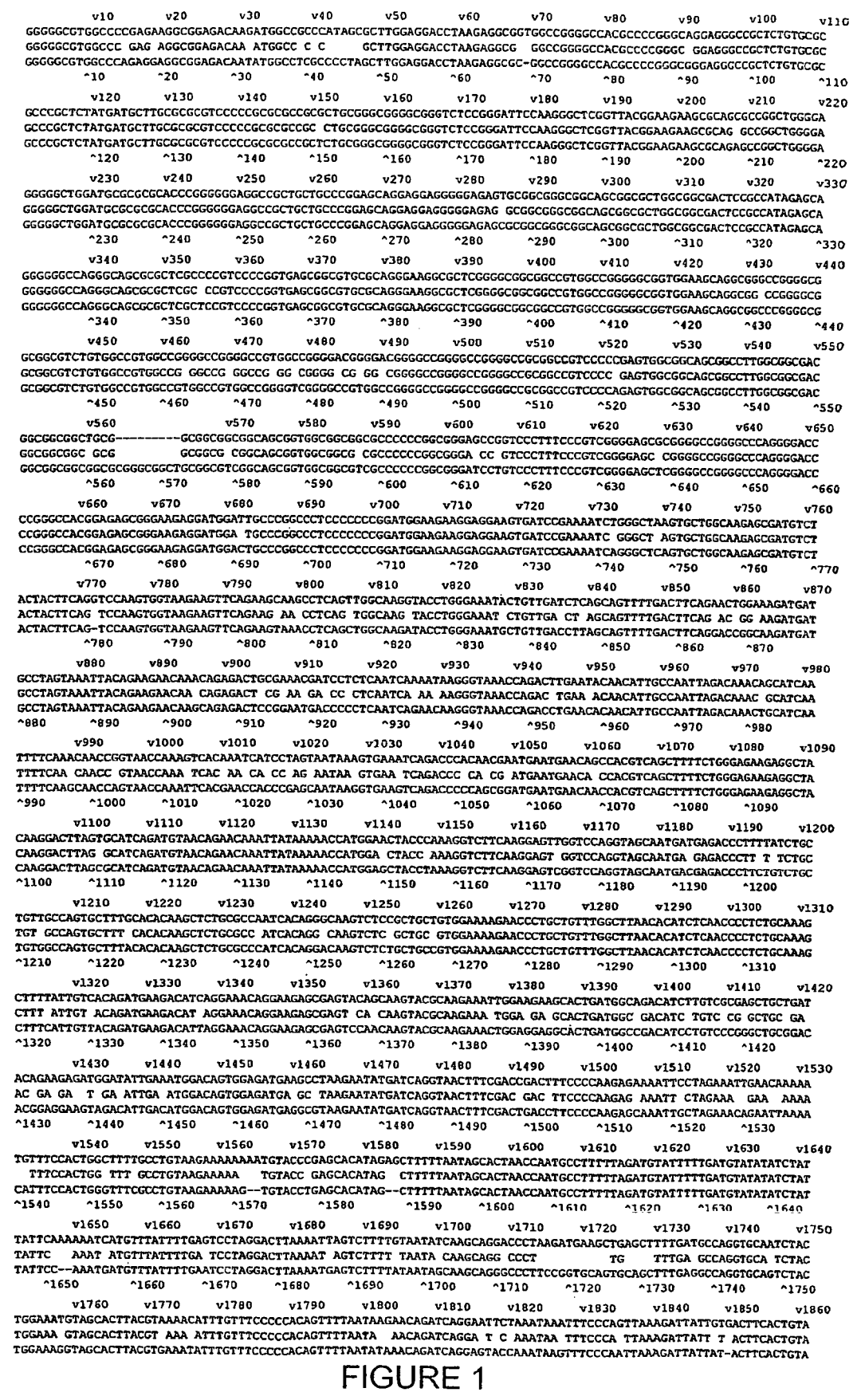

FIG. 1 presents an alignment of the nucleic acid sequences for demethylase 1 (dMTase 1 or MBD2) cDNA from human (top line; SEQ ID NO:1) and mouse (lower line; SEQ ID NO:3). The coding strand is shown. The centre line shows the consensus sequence.

FIG. 2 presents an alignment of the amino acid sequence of demethylase 1 (dMTase 1 or MBD2) from human (top line; SEQ ID NO:2) and mouse (lower line; SEQ ID NO:4). The centre line shows the consensus sequence.

DETAILED DESCRIPTION OF THE INVENTION

Figure 3:
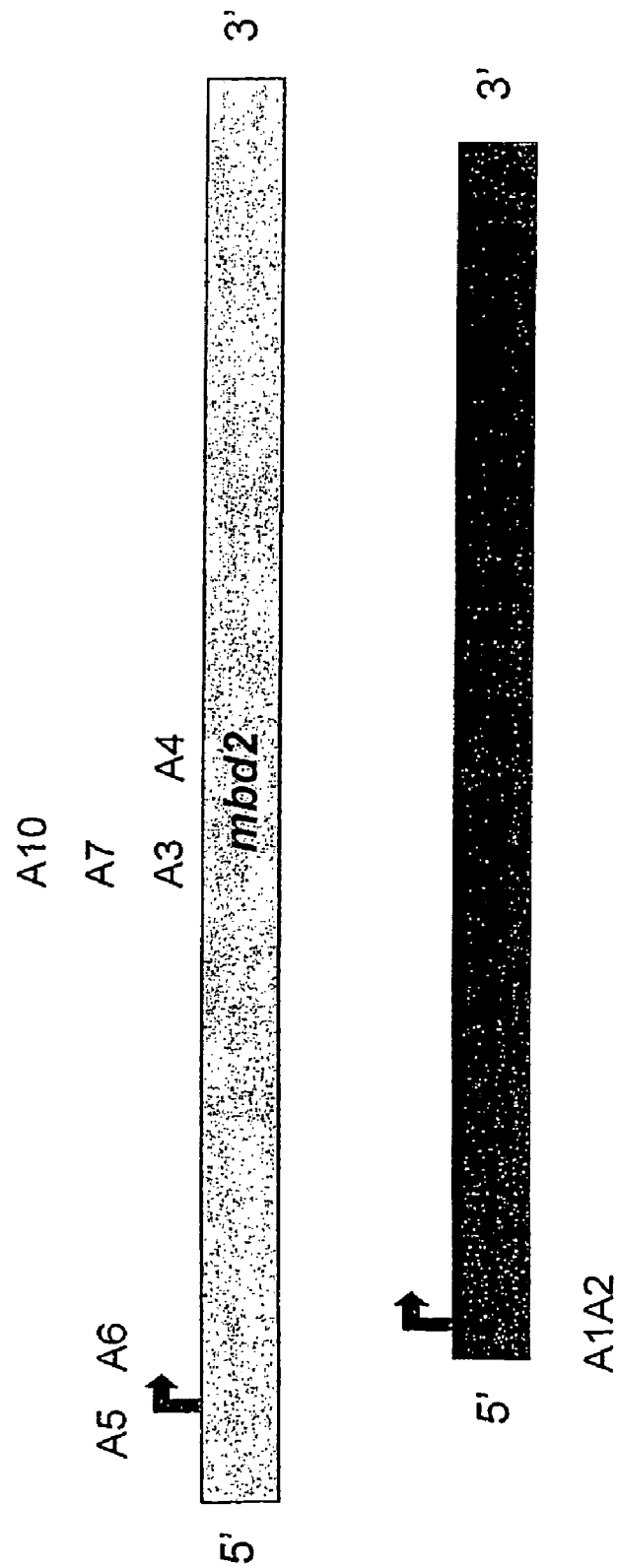
FIG. 3 depicts the nucleic acid sequences for antisense oligonucleotides A1 [SEQ ID NO: 5], A2 [SEQ ID NO: 6], A3 [SEQ ID NO: 7], A4 [SEQ ID NO: 8], A5 [SEQ ID NO: 9], A6 [SEQ ID NO: 10], A7 [SEQ ID NO: 11] and A10 [SEQ ID NO: 12], and their positions relative to the MBD2/dMTase open reading frames.

The present invention provides oligonucleotide inhibitors of MBD2/dMTase. The oligonucleotide inhibitors inhibit expression of the mbd2/dMTase gene and decrease the growth of tumour cells in vitro and in vivo. The oligonucleotide inhibitors of MBD2/dMTase provided by the present invention are thus useful in anti-cancer therapy.

Inhibition of MBD2/dMTase affects the expression of other genes that may be involved in the growth and/or proliferation of tumour cells, Therefore, the present invention further provides for methods to identify other genes that are potential targets for cancer therapy or diagnosis using the oligonucleotide inhibitors.

Definitions

Unless defined otherwise, all technical and scientific terms used herein have the same meaning as commonly understood by one of ordinary skill in the art to which this invention pertains.

The term "corresponds to" as used herein with reference to nucleic acid sequences means a polynucleotide sequence that is identical to all or a portion of a reference polynucleotide sequence. In contradistinction, the term "complementary to" is used herein to mean that the polynucleotide sequence is identical to all or a portion of the complement of a reference polynucleotide sequence. For illustration, the nucleotide sequence "TATAC" corresponds to a reference sequence "TATAC" and is complementary to a reference sequence "GTATA."

The following terms are used herein to describe the sequence relationships between two or more polynucleotides: "reference sequence," "window of comparison," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA or gene sequence, or may comprise a complete cDNA or gene sequence. Generally, a reference sequence is at least 20 nucleotides in length, and often at least 50 nucleotides in length.

A "window of comparison", as used herein, refers to a conceptual segment of the reference sequence of at least 15 contiguous nucleotide positions wherein a polynucleotide sequence may be compared to a reference sequence of at least 15 contiguous nucleotides and wherein the portion of the polynucleotide sequence in the window of comparison may comprise additions or deletions (i.e. gaps) of 20 percent or less as compared to the reference sequence (which does not comprise additions or deletions) for optimal alignment of the two sequences. Optimal alignment of sequences for aligning a comparison window may be conducted using the local homology algorithm of Smith and Waterman (1981) *Adv. Appl. Math.* 2:482, the homology alignment algorithm of Needleman and Wunsch (1970) *J. Mol. Biol.* 48:443, the search for similarity method of Pearson and Lipman (1988) *Proc. Natl. Acad. Sci.* (U.S.A.) 85:2444, or computerized implementations of these algorithms (GAP, BESTFIT, FASTA, and TFASTA in the Wisconsin Genetics Software Package Release 7.0, Genetics Computer Group, 573 Science Dr., Madison, Wis.), or by inspection. The best alignment (i.e. resulting in the highest percentage of identity over the comparison window) generated by the various methods is then selected.

The term "sequence identity" means that two polynucleotide sequences are identical (i.e. on a nucleotide-by-nucleotide basis) over the window of comparison. The term "percentage of sequence identity" is calculated by comparing two optimally aligned sequences over the window of comparison, determining the number of positions at which the identical nucleotide (e.g. A, T, C, G, U, or I) occurs in both sequences to yield the number of matched positions, dividing the number of matched positions by the total number of positions in the window of comparison (i.e. the window size), and multiplying the result by 100 to yield the percentage of sequence identity.

The term "substantial identity" as used herein denotes a characteristic of a polynucleotide sequence, wherein the polynucleotide comprises a sequence that has at least 50 percent sequence identity as compared to a reference sequence over the window of comparison.

MBD2/DNA Demethylase (MBD2/dMTase)

The oligonucleotide inhibitors according to the present invention are targeted to a mammalian MBD2/dMTase gene. The sequences for MBD2/dMTase genes isolated from human and from mouse are known in the art (see, for example, International Patent Application WO99/24583 and Genbank Accession Nos NM_003927 and NM_015832 (human) and NM 010773 (mouse)) and are provided herein (MBD2/dMTase 1, SEQ ID NOs: 1, 3 and 15). Other MBD2/dMTase gene sequences can be readily obtained by one skilled in the art, for example, by conducting BLASTN searches of GenBank or other publicly available databases using the sequences provided herein, or by standard molecular biology techniques utilising isolated cellular DNA or RNA, or commercially available cDNA libraries, and the sequences provided herein, or portions thereof, as hybridization probes.

In one embodiment of the present invention, the oligonucleotide inhibitors are targeted to a human MBD2/dMTase 1 gene. In another embodiment, the oligonucleotide inhibitors are targeted to the human MBD2/dMTase 1 gene shown in SEQ ID NOs: 1 or 15. Ina further embodiment, the oligonucleotide inhibitors are targeted to the mouse MBD2/dMTase 1 gene [SEQ ID NO:3].

Oligonucleotide Inhibitors of MBD2/dMTase

In the context of the present invention, the term "oligonucleotide inhibitor" encompasses antisense oligonucleotides, short interfering RNA (siRNA) molecules and ribozymes.

The term "oligonucleotide" as used herein refers to an oligomer or polymer of ribonucleic acid (RNA), deoxyribonucleic acid (DNA), or modified versions thereof, or RNA or DNA mimetics. This term, therefore, includes oligonucleotides composed of naturally occurring nucleobases, sugars and covalent internucleoside (backbone) linkages as well as oligonucleotides having non-naturally-occurring portions, which function similarly. Such modified or substituted oligonucleotides are often preferred over native forms because of desirable properties such as, for example, enhanced cellular uptake, enhanced affinity for the nucleic acid target and increased stability in the presence of nucleases. The term also includes chimeric oligonucleotides. Chimeric oligonucleotides are oligonucleotides that contain two or more chemically distinct regions, each region comprising at least one monomer unit. The oligonucleotides according to the present invention can be single-stranded or they can be double-stranded.

As is known in the art, a nucleoside is a base-sugar combination and a nucleotide is a nucleoside that further includes a phosphate group covalently linked to the sugar portion of the nucleoside. In forming oligonucleotides, the phosphate groups covalently link adjacent nucleosides to one another to form a linear polymeric compound, with the normal linkage or backbone of RNA and DNA being a 3' to 5' phosphodiester linkage. The oligonucleotide inhibitors of the invention include those containing modified backbones or non-natural internucleoside linkages. As defined herein, oligonucleotides having modified backbones include both those that retain a phosphorus atom in the backbone and those that lack a phosphorus atom in the backbone. For the purposes of the present invention, and as sometimes referenced in the art, modified oligonucleotides that do not have a phosphorus atom in their internucleoside backbone can also be considered to be oligonucleotides.

Exemplary modified oligonucleotide backbones that can be incorporated into the oligonucleotides according to the present invention include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogues of these, and analogues having inverted polarity wherein the adjacent pairs of nucleoside units are linked 3'-5' to 5'-3' or 2'-5' to 5'-2'. Various salts, mixed salts and free acid forms are also included.

Exemplary modified oligonucleotide backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include morpholino linkages (formed in part from the sugar portion of a nucleoside); siloxane backbones; sulphide, sulphoxide and sulphone backbones; formacetyl and thioformacetyl backbones; methylene formacetyl and thioformacetyl backbones; alkene containing backbones; sulphamate backbones; methyleneimino and methylenehydrazino backbones; sulphonate and sulphonamide backbones; amide backbones; and others having mixed N, O, S and $CH_2$, component parts.

The term "alkyl" as used herein refers to monovalent alkyl groups having from 1 to 20 carbon atoms. In one embodiment of the present invention, the alkyl group has between 1 and 6 carbon atoms. Examples of suitable alkyl groups include, but are not limited to, methyl, ethyl, n-propyl, iso-propyl, n-butyl, iso-butyl, n-hexyl, and the like.

The term "cycloalkyl" refers to cyclic all groups of from 3 to 20 carbon atoms having a single cyclic ring or multiple condensed rings. Examples of suitable cycloalkyl groups include, but are not limited to, single ring structures such as cyclopropyl, cyclobutyl, cyclopentyl, cyclooctyl, and the like, or multiple ring structures such as adamantanyl, and the like.

The present invention also contemplates oligonucleotide mimetics in which both the sugar and the internucleoside linkage of the nucleotide units are replaced with novel groups. The base units are maintained for hybridization with an appropriate nucleic acid target. An example of such an oligonucleotide mimetic, which has been shown to have excellent hybridization properties, is a peptide nucleic acid (PNA) [Nielsen et al., *Science*, 254:1497-1500 (1991)]. In PNA compounds, the sugar-backbone of an oligonucleotide is replaced with an amide-containing backbone, in particular an aminoethylglycine backbone. The nucleobases are retained and are bound directly or indirectly to aza-nitrogen atoms of the amide portion of the backbone.

The present invention also contemplates oligonucleotides comprising "locked nucleic acids" (LNAs), which are conformationally restricted oligonucleotide analogues containing a methylene bridge that connects the 2'-O of ribose with the 4'-C (see, Singh et al., *Chem. Commun.*, 1998, 4:455-456). LNA and LNA analogues display very high duplex thermal stabilities with complementary DNA and RNA, stability towards 3'-exonuclease degradation, and good solubility properties. Synthesis of the LNA analogues of adenine, cytosine, guanine, 5-methylcytosine, thymine and uracil, their oligomerization, and nucleic acid recognition properties have been described (see Koshkin et al., *Tetrahedron*, 1998, 54:3607-3630). Studies of mismatched sequences show that LNA obey the Watson-Crick base pairing rules with generally improved selectivity compared to the corresponding unmodified reference strands. Antisense oligonucleotides containing LNAs have been described (Wahlestedt et al., *Proc. Natl. Acad. Sci. U.S.A.*, 2000, 97:5633-5638), which were efficacious and non-toxic. In addition, the LNA/DNA copolymers were not degraded readily in blood serum and cell extracts.

LNAs form duplexes with complementary DNA or RNA or with complementary LNA, with high thermal affinities. The universality of LNA-mediated hybridization has been emphasized by the formation of exceedingly stable LNA:LNA duplexes (Koshkin et al, *J. Am. Chem. Soc.*, 1998, 120:13252-13253). LNA:LNA hybridization was shown to be the most thermally stable nucleic acid type duplex system, and the RNA-mimicking character of LNA was established at the duplex level. Introduction of three LNA monomers (T or A) resulted in significantly increased melting points toward DNA complements.

Synthesis of 2'-amino-LNA (Singh et al., J. Org. Chem., 1998, 63, 10035-10039) and 2'-methylamino-LNA has been described and thermal stability of their duplexes with complementary RNA and DNA strands reported. Preparation of phosphorothioate-LNA and 2'-thio-LNA have also been described (Kumar et al., *Bioorg. Med. Chem. Lett.*, 1998, 8:2219-2222).

Modified oligonucleotides according to the present invention may also contain one or more substituted sugar moieties. For example, oligonucleotides may comprise sugars with one of the following substituents at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Examples of such groups are: $O[(CH_2)_n O]_m CH_3$, $O(CH_2)_n OCH_3$, $O(CH_2)_n NH_2$, $O(CH_2)_n CH_3$, $O(CH_2)_n ONH_2$, and $O(CH_2)_n ON[(CH_2)_n CH_3)]_2$, where n and m are from 1 to about 10. Alternatively, the oligonucleotides may comprise one of the following substituents at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2 CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Specific examples include 2'-O-methyl (2'-O—$CH_3$), 2'-methoxyethoxy (2'-O—$CH_2$ $CH_2$ $OCH_3$, also known as 2'-O-(2-methoxyethyl) or 2'-MOE) [Martin et al., *Helv. Chim. Acta*, 78:486-504(1995)], 2'-dimethylaminooxyethoxy (2'-$O(CH_2)_2$ $ON(CH_3)_2$ group, also known as 2'-DMAOE), 2'-aminopropoxy (2'-$OCH_2$ $CH_2$ $CH_2 NH_2$) and 2'-fluoro (2'-F).

Similar modifications may also be made at other positions on the oligonucleotide, for example at the 3' position of the sugar on the 3' terminal nucleotide or in 2'-5' linked oligonucleotides and the 5' position of 5' terminal nucleotide. Oligonucleotides may also comprise sugar mimetics such as cyclobutyl moieties in place of the pentofuranosyl sugar.

Oligonucleotides according to the present invention may also include modifications or substitutions to the nucleobase. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C); inosine; 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine and 2-thiocytosine; 5-halouracil and cytosine; 5-propynyl uracil and cytosine; 6-azo uracil, cytosine and thymine; 5-uracil (pseudouracil); 4-thiouracil; 8-halo, 8-amino, 8-thiol, 8-thioalkyl, 8-hydroxyl and other 8-substituted adenines and guanines; 5-halo particularly 5-bromo, 5-trifluoromethyl and other 5-substituted uracils and cytosines; 7-methylguanine and 7-methyladeninie; 8-azaguanine and 8-azaadenine; 7-deazaguanine and 7-deazaadenine; 3-deazaguanine and 3-deazaadenine. Further nucleobases include those disclosed in U.S. Pat. No. 3,687,808; The Concise Encyclopaedia Of Polymer Science And Engineering, (1990) pp 858-859, Kroschwitz, J. I., ed. John Wiley & Sons; Englisch et al., *Angewandte Chemie, Int. Ed.*, 30:613 (1991); and Sanghvi, Y. S., (1993) *Antisense Research and Applications*, pp 289-302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi, Y. S., (1993) *Antisense Research and Applications*, pp 276-278, Crooke, S. T. and Lebleu, B., ed., CRC Press, Boca Raton].

Another oligonucleotide modification included in the present invention is the chemical linkage to the oligonucleotide of one or more moieties or conjugates which enhance the activity, cellular distribution or cellular uptake of the oligonucleotide. Such moieties include, but are not limited to, lipid moieties such as a cholesterol moiety [Letsinger et al., *Proc. Natl. Acad. Sci. USA*, 86:6553-6556 (1989)], cholic acid [Manoharan et al., *Bioorg. Med. Chem. Let.*, 4:1053-1060 (1994)], a thioether, e.g. hexyl-S-tritylthiol [Manoharan et al., *Ann. N.Y. Acad. Sci.*, 660:306-309 (1992); Manoharan et al., *Bioorg. Med. Chem. Lett.*, 3:2765-2770 (1993)], a thio-cholesterol [Oberhauser et al., *Nucl. Acids Res.*, 20:533-538 (1992)], an aliphatic chain, e.g. dodecandiol or undecyl residues [Saison-Behmoaras et al., *EMBO J.*, 10:1111-1118 (1991); Kabanov et al., *FEBS Lett.*, 259:327-330 (1990); Svinarchuk et al., *Biochimie*, 75:49-54 (1993)], a phospholipid, e.g. di-hexadecyl-rac-glycerol or triethylammonium 1,2-di-O-hexadecyl-rac-glycero-3-H-phosphonate [Manoharan et al., *Tetrahedron Lett.*, 36:3651-3654 (1995); Shea et al., *Nucl. Acids Res.*, 18:3777-3783 (1990)], a polyamine or a polyethylene glycol chain [Manoharan et al., *Nucleosides & Nucleotides*, 14:969-973 (1995)], or adamantane acetic acid [Manoharan et al., *Tetrahedron Lett.*, 36:3651-3654 (1995)], a palmityl moiety [Mishra et al., *Biochim. Biophys. Acta*, 1264:229-237 (1995)], or an octadecylamine or hexylamino-carbonyl-oxycholesterol moiety [Crooke et al., *J. Pharmacol. Exp. Ther.*, 277:923-937 (1996)].

One skilled in the art will recognise that it is not necessary for all positions in a given oligonucleotide to be uniformly modified. The present invention, therefore, contemplates the incorporation of more than one of the aforementioned modifications into a single oligonucleotide or even at a single nucleoside within the oligonucleotide.

As indicated above, oligonucleotides that are chimeric compounds are included within the scope of the present invention. Chimeric oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids.

In the context of the present invention, an oligonucleotide is "nuclease resistant" when it has either been modified such that it is not susceptible to degradation by DNA and RNA nucleases or, alternatively, has been placed in a delivery vehicle which itself protects the oligonucleotide from DNA or RNA nucleases. Nuclease resistant oligonucleotides include, for example, methyl phosphonates, phosphorothioates, phosphorodithioates, phosphotriesters, and morpholino oligomers. Suitable delivery vehicles for conferring nuclease resistance include, for example, liposomes.

The present invention further contemplates oligonucleotides that contain groups for improving the pharmacokinetic and/or pharmacodynamic properties of the oligonucleotide.

i) Antisense Oligonucleotides

The term "antisense oligonucleotide" as used herein indicates an oligonucleotide having a nucleotide sequence that is complementary to a portion of the mRNA transcribed from the gene of interest. In the context of the present invention, the gene of interest is the gene encoding a mammalian MBD2/dMTase.

Antisense oligonucleotides are targeted to specific nucleic acids. "Targeting" an antisense oligonucleotide to a particular nucleic acid, in the context of the present invention, is a multistep process that usually begins with the identification of a nucleic acid sequence whose function is to be modulated. In the context of the present invention, the target is the gene encoding a mammalian MBD2/dMTase, or the mRNA transcribed from a mammalian MBD2/dMTase gene. As described above, sequences for mammalian MBD2/dMTase genes are known in the art or are readily obtainable. The targeting process also includes determination of a site, or sites, within this nucleic acid sequence for the antisense interaction to occur such that the desired effect, i.e. modulation of expression of the gene, will result. Once the target site, or sites, has been identified, oligonucleotides are chosen that are sufficiently complementary (i.e. hybridize with sufficient strength and specificity) to the target to give the desired result.

Generally, there are five regions of a gene that may be targeted for antisense modulation: the 5' untranslated region (5'-UTR), the translation initiation (or start) codon region, the open reading frame (ORF), the translation termination (or stop) codon region and the 3' untranslated region (3'-UTR).

The terms "translation initiation codon" and "start codon" can encompass many codon sequences, even though the initiator amino acid in each instance is typically methionine in eukaryotes. It is also known in the art that eukaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding MBD2/dMTase regardless of the sequence(s) of such codons.

As is known in the art, some eukaryotic transcripts are directly translated, however, most mammalian genes, or open reading frames (ORFs), contain one or more sequences, known as "introns," which are excised from a transcript before it is translated. The expressed (unexcised) portions of the ORF are referred to as "exons" and are spliced together to form an mRNA transcript (Alberts et al., (1983) *Molecular Biology of the Cell*, Garland Publishing Inc., New York, pp. 411-415). In the context some instances, an ORF may also contain one or more sites that may be targeted for antisense due to some functional significance in vivo. Examples of the latter types of sites include intragenic stem-loop structures (see, for example, U.S. Pat. No. 5,512,438) and, in unprocessed mRNA molecules (primary transcripts), intron/exon splice sites. As is known in the art, primary RNA transcripts can be alternatively processed in vivo depending on the splicing of the exons and can, therefore, give rise to alternatively spliced mRNA molecules which correspond to the same gene but differ in structure. In addition, mRNA molecules possess a 5' cap region that may also serve as a target for antisense. The 5' cap of a mRNA comprises an $N^7$-methylated guanosine residue joined to the 5'-most residue of the mRNA via a 5'-5' triphosphate linkage. The 5' cap region of a mRNA is considered to include the 5' cap structure itself as well as the first approximately 50 nucleotides adjacent to the cap.

Thus, the antisense oligonucleotides according to the present invention can be complementary to regions of a complete MBD2/dMTase gene including the introns, to the primary mRNA transcript of a MBD2/dMTase gene or to one or more of the final, spliced versions of the mRNA from a MBD2/dMTase gene.

The antisense oligonucleotides in accordance with the present invention are selected from a sequence complementary to a mammalian MBD2/dMTase gene such that the sequence exhibits the least likelihood of forming duplexes, hair-pins, or of containing homooligomer/sequence repeats. One skilled in the art will appreciate that these properties can be determined qualitatively using various computer modeling programs, for example, the program OLIGO® Primer Analysis Software, Version 5.0 (distributed by National Biosciences, Inc., Plymouth, Minn.).

The oligonucleotide may further contain a GC clamp. The oligonucleotides may also comprise a TCCC motif. The presence of such a motif in an antisense oligonucleotide has been shown increase the likelihood that the mRNA:DNA duplex will undergo RNase H-mediated degradation. RNase H is a cellular endonuclease that cleaves the RNA strand of an RNA:DNA duplex. In antisense therapy, therefore, activation of RNase H results in cleavage of the mRNA target, thereby greatly enhancing the efficiency of oligonucleotide inhibition of gene expression.

Antisense oligonucleotides can also be selected that are complementary to a nucleic acid sequence which constitutes a region of a MBD2/dMTase gene that is highly conserved between the MBD2/dMTase genes of two or more species. These properties can be determined, for example, using the BLASTN program (Altschul, et al., (1990) *J. Mol. Biol.*, 215:403-10) of the University of Wisconsin Computer group (GCG) software (Devereux. et al., (1984) *Nucleic Acids Res.*, 12:387-395) with the National Center for Biotechnology Information (NCBI) databases.

It is understood in the art that an antisense oligonucleotide need not have 100% identity with the complement of its target sequence in order to be effective. The antisense oligonucleotides in accordance with the present invention, therefore, have a sequence that is at least about 60% identical to the complement of the target sequence. In one embodiment of the present invention, the antisense oligonucleotides have a sequence that is at least about 70% identical to the complement of the target sequence. In another embodiment, the antisense oligonucleotides have a sequence that is at least about 80% identical to the complement of the target sequence. In other embodiments, they have a sequence that is at least about 90% identical or at least about 95% identical to the complement of the target sequence. Identity can be determined, for example, by using the BLASTN program of the University of Wisconsin Computer Group (GCG) software and allows for gaps or mismatches of several bases.

In order for the antisense oligonucleotides of the present invention to function in inhibiting expression of the MBD2/dMTase gene, it is necessary that they demonstrate adequate specificity for the target sequence and do not bind to other nucleic acid sequences in the cell. Therefore, in addition to possessing an appropriate level of sequence identity to the complement of the target sequence, the antisense oligonucleotides of the present invention should not closely resemble other known sequences. The antisense oligonucleotides of the present invention, therefore, should be less than 50% identical to any other mammalian nucleic acid sequence. The identity of the antisense oligonucleotides of the present invention to other sequences can be determined, for example, through the use of the BLASTN program and the NCBI databases as indicated above.

The antisense oligonucleotides according to the present invention typically between about 7 and about 100 nucleotides in length. In one embodiment, the antisense oligonucleotides comprise from about 7 to about 50 nucleotides, or nucleotide analogues. In another embodiment, the antisense oligonucleotides comprise from about 12 to about 50 nucleotides, or nucleotide analogues. In other embodiments the antisense oligonucleotides comprise from about 7 to about 35 nucleotides, or nucleotide analogues, from about 12 to about 35 nucleotides, or nucleotide analogues, and from about 18 to about 25 nucleotides, or nucleotide analogues.

In a further embodiment of the present invention, the antisense oligonucleotides comprise at least 7 consecutive nucleotides from a nucleic acid sequence as set forth in any one of SEQ ID NOs: 5-12, or an analogue thereof.

TABLE 1

Antisense oligonucleotides to mbd2/dMTase

| Antisense oligonucleotide | Sequence | SEQ ID NO |
|---|---|---|
| A1 | 5'-GGCAATCCATCCTCTTCC-3' | 5 |
| A2 | 5'-CTTCCTCCTTCTTCCATC-3' | 6 |
| A3 | 5'-CAACAGTATTTCCCAGG-3' | 7 |
| A4 | 5'-TGTAGCCTCTTCTCCCA-3' | 8 |
| A5 | 5'-ATCCAGCCCCTCCCCAG-3' | 9 |
| A6 | 5'-CACTCTCCCCCTCCCCCT-3' | 10 |
| A7 | 5'-TCAACAGTATTTCCCAGGTA-3' | 11 |
| A10 | 5'-UCAACAGTATTTCCCAGGUA-3' | 12 |

In another embodiment of the present invention, the antisense oligonucleotides comprise one or more phosphorothioate backbone linkages. In still another embodiment, all backbone linkages in the antisense oligonucleotide are phosphorothioate linkages. In yet another embodiment of the present invention, the antisense oligonucleotides are chimeric molecules comprising one or more phosphorothioate backbone linkages and one or more 2'-O-methyl modified bases.

ii) Short Interfering RNA (siRNA) Molecules

RNA interference mediated by short interfering double-stranded RNA molecules (siRNA) is known in the art to play an important role in post-transcriptional gene silencing [Zamore, *Nature Struc. Biol.*, 8:746-750 (2001)]. siRNA molecules are typically 21-22 base pairs in length and are generated in nature when long double-stranded RNA molecules are cleaved by the action of an endogenous ribonuclease. Recently, it has been demonstrated that transfection of mammalian cells with synthetic siRNA molecules having a sequence identical to a target gene leads to a reduction in the mRNA levels of the target gene [Elbashir, et al., *Nature*, 411:494-498 (2001)].

The oligonucleotide inhibitors according to the present invention can be siRNA molecules which are targeted to a mammalian MBD2/dMTase gene such that the sequence of the siRNA corresponds to a portion of the MBD2/dMTase gene. As is known in the art, effective siRNA molecules are typically less than 30 base pairs in length to help prevent them triggering non-specific RNA interference pathways in the cell via the interferon response. In accordance with the present invention, the siRNA molecules are between about 15 and about 30 nucleotides in length. In one embodiment, the siRNA molecules are between about 15 and about 25 base pairs in length. In another embodiment, they are between 19 and 22 base pairs in length.

The double-stranded siRNA molecules can further comprise poly-T or poly-U overhangs at the 3' and 5' ends to minimise RNase-mediated degradation of the molecules. Thus, in another embodiment of the present invention, the siRNA molecules comprise overhangs at the 3' and 5' ends which consist of two thymidine or two uridine residues. Design and construction of siRNA molecules is known in the art [see, for example, Elbashir, et al., *Nature*, 411:494-498 (2001); Bitko and Barik, *BMC Microbiol.*, 1:34 (2001)]. In addition, kits that provide a rapid and efficient means of constructing siRNA molecules by in vitro transcription are also commercially available (Ambion, Austin, Tex.; New England Biolabs, Beverly, Mass.) and may be used to construct the siRNA molecules according to the present invention.

iii) Ribozymes

The oligonucleotide inhibitors according to the present invention can be ribozymes that specifically target mRNA encoding a mammalian MBD2/dMTase. As is known in the art, ribozymes are RNA molecules having an enzymatic activity that enables the ribozyme to repeatedly cleave other separate RNA molecules in a nucleotide-sequence specific manner. Such enzymatic RNA molecules can be targeted to virtually any mRNA transcript, and efficient cleavage can be achieved in vitro [Kim et al., *Proc. Natl. Acad. Sci. USA*, 84:8788, (1987); Haseloff and Gerlach, *Nature*, 334:585, (1988); Cech, *JAMA*, 260:3030, (1988); Jefferies et al., *Nucleic Acids Res.*, 17:1371, (1989)].

Typically, a ribozyme comprises two portions held in close proximity, a mRNA binding portion having a sequence complementary to the target mRNA sequence, and a catalytic portion which acts to cleave the target mRNA. A ribozyme acts by first recognising and binding a target mRNA by complementary base-pairing through the target mRNA binding portion of the ribozyme. Once it is specifically bound to its target, the ribozyme catalyses cleavage of the target mRNA. Such strategic cleavage destroys the ability of a target mRNA to direct synthesis of an encoded protein. Having bound and cleaved its mRNA target, the ribozyme is released and can repeatedly bind and cleave new target mRNA molecules.

One of the best characterised ribozyme molecules is the "hammerhead ribozyme." Hammerhead ribozymes comprise a hybridizing region which is complementary in nucleotide sequence to at least part of the target mRNA, and a catalytic region which is adapted to cleave the target mRNA. In general, the hybridizing region contains at least 9 nucleotides. The present invention therefore contemplates the use of the oligonucleotide inhibitors as part of the hybridizing region of a hammerhead ribozyme, wherein the hybridizing region comprises at least 9 nucleotides that are complementary to a gene encoding MBD2/dMTase and is joined to an appropriate catalytic domain. The construction and production of such ribozymes is well-known in the art [see, for example, Haseloff and Gerlach; *Nature*, 334:585-591(1988)].

Ribozymes in accordance with the present invention also include RNA endoribonucleases (hereinafter "Cech-type ribozymes") such as the one that occurs naturally in *Tetrahymena thermophila* (known as the IVS, or L-19 IVS RNA), which have been extensively described in the literature [see, Zaug, et al., *Science*, 224:574-578 (1984); Zaug and Cech, *Science*, 231:470-475 (1986); Zaug, et al., *Nature*, 324:429-433 (1986); U.S. Pat. No. 4,987,071; Been and Cech, *Cell*, 47:207-216 (1986)]. Cech-type ribozymes comprise an 8 nucleotide active site which hybridizes to a target mRNA sequence with subsequent cleavage of the target mRNA by the ribozyme.

One skilled in the art will understand that there is a narrow range of binding free-energies between a ribozyme and its substrate that will produce maximal ribozyme activity. Such binding energy can be optimized by making ribozymes with G to I (inosine) and U to BrU (bromouracil) substitutions (or equivalent substitutions as known in the art) in the mRNA binding portion. Such substitutions allow manipulation of the binding free-energy without altering the target recognition sequence, the length of the mRNA binding portion, or the enzymatic portion of the ribozyme. The shape of the free-energy vs. ribozyme activity curve can be readily determined using data from standard experiments known in the art in which each base (or several bases) is modified or unmodified, and without the complication of changing the size of the ribozyme/substrate interaction.

If necessary, such experiments can be used to indicate the most active ribozyme structure. The use of modified bases thus permits "fine tuning" of the binding free energy to assure maximal ribozyme activity and is considered to be within the scope of the present invention. In addition, replacement of such bases, e.g., I for G, may permit a higher level of substrate specificity when cleavage of non-target RNA is a problem.

Preparation of the Oligonucleotide Inhibitors

The oligonucleotide inhibitors of the present invention can be prepared by conventional techniques well-known to those skilled in the art. For example, the oligonucleotides can be prepared using solid-phase synthesis using commercially available equipment, such as the equipment available from Applied Biosystems Canada Inc. (Mississauga, Canada). As is well-known in the art, modified oligonucleotides, such as phosphorothioates and alkylated derivatives, can also be readily prepared by similar methods.

Alternatively, the oligonucleotide inhibitors of the present invention can be prepared by enzymatic digestion and/or amplification of the naturally occurring MBD2/dMTase gene or mRNA, or of cDNA synthesized from the mRNA, using standard techniques known in the art. When the oligonucleotide inhibitors comprise RNA, they can be prepared by in vitro transcription methods also known in the art. As indicated above, siRNA molecules can also be conveniently prepared using commercially available in vitro transcription kits.

Oligonucleotides can also be prepared using recombinant DNA techniques. The present invention, therefore, encompasses expression vectors comprising nucleic acid sequences that encode the oligonucleotide inhibitors and subsequent expression of the encoded oligonucleotides in a suitable host cell. Such expression vectors can be readily constructed using procedures known in the art [see, for example, Ausubel, et al., *Current Protocols in Molecular Biology*, John Wiley & Sons, Inc, NY. (1989 and updates)]. Examples of suitable vectors include, but are not limited to, plasmids, phagemids, cosmids, bacteriophages, baculoviruses, retroviruses, and DNA viruses. One skilled in the art will understand that selection of the appropriate host cell for expression of the antisense oligonucleotide will be dependent upon the vector chosen. Examples of suitable host cells include, but are not limited to, bacterial, yeast, insect, plant and mammalian cells.

The selected expression vector may further include regulatory elements, such as transcriptional elements, required for efficient transcription of the oligonucleotide sequences. Examples of regulatory elements that can be incorporated into the vector include, but are not limited to, promoters, enhancers, terminators, and polyadenylation signals. The present invention, therefore, provides vectors comprising a regulatory element operatively linked to a nucleic acid sequence encoding an oligonucleotide inhibitor. One skilled in the art will appreciate that selection of suitable regulatory elements is dependent on the host cell chosen for expression of the oligonucleotide inhibitor and that such regulatory elements may be derived from a variety of sources, including bacterial, fungal, viral, mammalian or insect genes.

In the context of the present invention, the expression vector may additionally contain a reporter gene. Suitable reporter genes include, but are not limited to, β-galactosidase, green fluorescent protein, red fluorescent protein, luciferase, and β-glucuronidase. Incorporation of a reporter gene into the expression vector allows transcription of the oligonucleotide to be monitored by detection of a signal generated by expression of the reporter gene.

In accordance with the present invention, the expression vectors can be introduced into a suitable host cell or tissue by one of a variety of methods known in the art. Such methods can be found generally described in Sambrook et al, *Molecular Cloning: A Laboratory Manual*, Third Edition, Cold Spring Harbor Press, NY (2001) and Ausubel et al., *Current Protocols in Molecular Biology*, John Wiley & Sons, Inc, NY (1989 and updates) and include, for example, stable or transient transfection, lipofection, electroporation, and infection with recombinant viral vectors.

Ribozyme inhibitors comprising the oligonucleotides according to the present invention can be readily constructed by techniques known in the art. In these molecules the oligonucleotide sequence is included in the hybridizing or mRNA binding portion of the ribozyme and is joined to an appropriate catalytic portion. Selection of an appropriate catalytic portion is dependent on the type of ribozyme to be constructed and can be readily determined by one skilled in the art [see, for example, Haseloff and Gerlach, *Nature*, 334:585-591 (1988); U.S. Pat. No. 4,987,071].

Efficacy of the Oligonucleotide Inhibitors

The efficacy of the oligonucleotide inhibitors of the present invention in inhibiting the expression of a mammalian MBD2/dMTase gene or the growth of cancer cells can be determined by one or a combination of a number of different methods known in the art. Exemplary methods that can be used to determine the efficacy of the oligonucleotide inhibitors are provided below.

i) In Vitro Testing

If desired, initial determinations of the efficacy of the oligonucleotides of the present invention can be made using in vitro techniques.

For example, the ability of the oligonucleotide inhibitors to inhibit expression of a MBD2/dMTase gene can be determined by introducing the oligonucleotide into a cell line that normally expresses MBD2/dMTase. The amount of mRNA transcribed from the gene can then be measured by standard techniques, such as by Northern blot analysis. Alternatively, the amount of MBD2/dMTase protein produced by the cell can be measured, for example, by Western blot analysis. The specificity of the oligonucleotides for their mRNA target can be determined by conducting appropriate control experiments in parallel. The amount of mRNA or protein produced in a cell treated with the oligonucleotide can be compared with that produced in a control, untreated cell or a cell treated with a control oligonucleotide and provides an indication of how successfully the oligonucleotide has inhibited MBD2/dMTase gene expression. Appropriate controls will be dependent upon the type of oligonucleotide inhibitor being investigated and can be readily selected by one skilled in the art. Examples of appropriate controls include untreated cells and cells treated with randomised or "scrambled" oligonucleotides, oligonucleotides containing a defined number of mismatches, long non-specific double-stranded RNA molecules or ribozymes incorporating a randomised oligonucleotide in its mRNA binding domain.

In accordance with the present invention, the oligonucleotide inhibitors are selected based on their ability to decrease the expression of a MBD2/dMTase gene by at least about 50% when compared to an untreated control. In one embodiment, the oligonucleotide inhibitors decrease the expression of a MBD2/dMTase gene by at least about 60%. In another embodiment, the oligonucleotide inhibitors decrease the expression of a MBD2/dMTase gene by at least about 70%. In other embodiments, the oligonucleotide inhibitors decrease the expression of a MBD2/dMTase gene by at least about 80% and by at least 90%.

Alternatively, the ability of the oligonucleotide inhibitors to inhibit expression of MBD2/dMTase can be determined in vitro by assaying the total cellular activity of the MBD2/dMTase enzyme in the presence and absence of the oligonucleotide. For example, the demethylase activity of the MBD2/dMTase protein can be determined using a cell-based assay in which expression of a reporter gene present within the cell is dependent upon demethylation of the reporter gene DNA. For example, the vector CMV-GFP can be methylated in vitro and then transfected into cells, such as human embryonic kidney (HEK) cells, treated with the histone deacetylase inhibitor trichostatin A [Cervoni, N. & Szyf, M., (2001) *J. Biol. Chem.*, 276:40778-40787]. Demethylation of the vector DNA occurs within the cells through the action of the endogenous MBD2/dMTase. Whereas the methylated form of CMV-GFP is not expressed, the demethylated CMV-GFP is expressed and the resultant GFP protein can be readily detected by live fluorescence microscopy. Standard calculations using the amount of GFP produced can then be employed to determine the amount of vector DNA demethylated and thus, the activity of the MBD2/dMTase. One skilled in the art will recognise that other cell lines, reporter genes and detection methods known in the art can be used in this type of assay. For example, the reporter genes red fluorescent protein or luciferase may be used.

The oligonucleotide inhibitors can be further tested in vitro by determining their ability to inhibit anchorage-independent growth of tumour cells. Anchorage-independent growth is known in the art to be a good indicator of tumourigenicity. In general, anchorage-independent growth is assessed by plating cells from an appropriate cancer cell-line onto soft agar and determining the number of colonies formed after an appropriate incubation period. Growth of cells treated with the oligonucleotide inhibitor can then be compared with that of cells treated with an appropriate control (such as those as described above) and with that of untreated cells.

In accordance with the present invention, the oligonucleotide inhibitors decrease the anchorage-independent growth of cancer cells by at least 20%, when compared to untreated cells or cells treated with a control oligonucleotide. In one embodiment, the oligonucleotide inhibitors decrease the anchorage-independent growth of cancer cells by at least 30%. In another embodiment, the oligonucleotide inhibitors decrease the anchorage-independent growth of cancer cells by at least 40%. In other embodiments, they decrease the growth by at least 50% and at least 60%.

In one embodiment of the present invention, in vitro testing of the oligonucleotide inhibitors is conducted in a cancer cell-line that expresses high levels of MBD2/dMTase. In a related embodiment the cancer cell-line is a human cancer cell-line. Examples of suitable cancer cell-lines for in vitro testing of the oligonucleotide inhibitors of the present invention include, but are not limited to, non-small cell lung carcinoma cell-lines A549 and H1299, breast cancer cell-line MCF-7, colon cancer cell-lines CaCo, HCT116 and HT29, cervical cancer cell-line HeLa. Other examples of suitable cell-lines are known in the art.

Toxicity of the oligonucleotide inhibitors can also be initially assessed in vitro using standard techniques. For example, human primary fibroblasts can be treated in vitro with the oligonucleotide in the presence of a commercial lipid carrier such as lipofectamine. Cells are then tested at different time points following treatment for their viability using a standard viability assay, such as the trypan-blue exclusion assay. Cells are also assayed for their ability to synthesize DNA, for example, using a thymidine incorporation assay, and for changes in cell cycle dynamics, for example, using a standard cell sorting assay in conjunction with a fluorocytometer cell sorter (FACS).

ii) In vivo Testing

The ability of the oligonucleotide inhibitors to inhibit tumour growth or proliferation in vivo can be determined in an appropriate animal model. In general, current animal models for screening anti-tumour compounds are xenograft models, in which a human tumour has been implanted into an animal. Examples of xenograft models of human cancer include, but are not limited to, human solid tumour xenografts in mice, implanted by sub-cutaneous injection and used in tumour growth assays; human solid tumour isografts in mice, implanted by fat pad injection and used in tumour growth assays; experimental models of lymphoma and leukaemia in mice, used in survival assays, and experimental models of lung metastasis in mice.

The oligonucleotide inhibitors of the present invention can be administered to an appropriate xenograft animal model, for example, by bolus infusion. Alternatively, cells can be treated ex vivo with the oligonucleotide inhibitor and then the treated cells can be injected or implanted into the animal. The size of the tumour is then assessed over a suitable time period and compared to that in an untreated control animal, or an animal treated with a control oligonucleotide. After an appropriate period of time, the animals are sacrificed and the tissue histology, size and/or proliferation of the tumour assessed. At this time, analysis of MBD2/dMTase protein expression and mRNA expression may also be conducted using standard techniques as described above and elsewhere.

For example, the oligonucleotide inhibitors can be tested in vivo on solid tumours using mice that are subcutaneously grafted bilaterally with 30 to 60 mg of a tumour fragment on day 0. The animals bearing tumours are mixed before being subjected to the various treatments and controls. In the case of treatment of advanced tumours, tumours are allowed to develop to the desired size, animals having insufficiently developed tumours being eliminated. The selected animals are distributed at random to undergo the treatments and controls. Animals not bearing tumours may also be subjected to the same treatments as the tumour-bearing animals in order to be able to dissociate the toxic effect from the specific effect on the tumour. Treatment with the oligonucleotide inhibitors generally begins from 3 to 22 days after grafting, depending on the type of tumour, and the animals are observed every day. The different animal groups are weighed about 3 or 4 times a week until the maximum weight loss is attained, after which the groups are weighed at least once a week until the end of the trial.

The tumours are measured about 2 or 3 times a week until the tumour reaches a pre-determined size and/or weight, or until the animal dies if this occurs before the tumour reaches the pre-determined size/weight. The animals are then sacrificed and the tissue histology, size and/or proliferation of the tumour assessed.

For the study of the effect of the oligonucleotide inhibitors on leukaemias, the animals are grafted with a particular number of cells, and the anti-tumour activity is determined by the increase in the survival time of the treated mice relative to the controls.

To study the effect of the oligonucleotide inhibitors of the present invention on tumour metastasis, tumour cells are typically treated with the composition ex vivo and then injected into a suitable test animal. The spread of the tumour cells from the site of injection is then monitored over a suitable period of time.

TABLE 2

Examples of xenograft models of human cancer

| Cancer Model | Cell Type |
|---|---|
| Tumour Growth Assay Human solid tumour xenografts in mice (sub-cutaneous injection) | Prostate (PC-3, DU145) Breast (MDA-MB-231, MVB-9) Colon (HT-29) Lung (NCI-H460, NCI-H209) Pancreatic (ASPC-1, SU86.86) Pancreatic: drug resistant (BxPC-3) Skin (A2058, C8161) Cervical (SIHA, HeLa-S3) Cervical: drug resistant (HeLa S3-HU-resistance) Liver (HepG2) Brain (U87-MG) Renal (Caki-1, A498) Ovary (SK-OV-3) |
| Tumour Growth Assay Human solid tumour isografts in mice (fat pad injection) | Breast: drug resistant (MDA-CDDP-S4, MDA-MB435-To. 1) |
| Survival Assay Experimental model of lymphoma and leukaemia in mice | Human: Burkitts lymphoma (Non-Hodgkin's) (raji) Murine: erythroleukemia (CB7 Friend retrovirus-induced) |
| Experimental model of lung metastasis in mice | Human: melanoma (C8161) Murine: fibrosarcoma (R3) |

In vivo toxic effects of the oligonucleotides can be evaluated by measuring their effect on animal body weight during treatment and by performing haematological profiles and liver enzyme analysis after the animal has been sacrificed.

Applications i) Therapeutic Applications

The oligonucleotide inhibitors of the present invention can be used to inhibit the growth or proliferation of tumour cells in vitro or in vivo. The present invention, therefore, provides for the use of the oligonucleotide inhibitors as anti-cancer drugs.

The present invention further provides a method of inhibiting the growth of tumour cells in a subject by administering a therapeutically effective amount of one or more of oligonucleotide inhibitors. The oligonucleotide inhibitors of the present invention, therefore, can be used to treat, stabilize or prevent cancer. In this context, the oligonucleotides may exert cytotoxic or cytostatic effects that cause a reduction in the size of a tumour, slow or prevent an increase in the size of a tumour, increase the disease-free survival time between the disappearance of a tumour and its reappearance, prevent an initial or subsequent occurrence of a tumour (e.g. metastasis), or reduce an adverse symptom associated with a tumour.

The present invention provides for the use of the oligonucleotide inhibitors in prophylactic treatments to aid in the prevention of genetic cancers, such as familial colorectal cancers, breast cancers, and the like.

The present invention also contemplates the use of the oligonucleotide inhibitors as "sensitizing agents," which selectively inhibit the growth of cancer cells. In this case, the oligonucleotide alone does not have a cytotoxic effect on the cell, but selectively arrests or slows the growth of cancer cells. The oligonucleotide thus provides a means of weakening the cancer cells, and thereby facilitates the benefit from conventional anti-cancer therapeutics.

Thus, the present invention contemplates the administration to a subject of a therapeutically effective amount of one or more oligonucleotide inhibitors administered with one or more anti-cancer therapeutics. The oligonucleotides can be administered before, during or after treatment with the anti-cancer therapeutic. An "anti-cancer therapeutic" is a compound, composition or treatment that prevents or delays the growth and/or metastasis of cancer cells. Such anti-cancer therapeutics include, but are not limited to, chemotherapeutic drug treatment, radiation, gene therapy, hormonal manipulation, immunotherapy and antisense oligonucleotide therapy. Examples of useful chemotherapeutic drugs include, but are not limited to, bleomycin, neocarcinostatin, suramin, doxorubicin, taxol, mitomycin C and cisplatin. It is to be understood that anti-cancer therapeutics for use in the present invention also include novel compounds or treatments developed in the future.

Examples of cancers that can be treated, stabilized, or prevented in accordance with the present invention include, but are not limited to, breast carcinomas, colon carcinomas, colorectal carcinomas, neuroblastomas, and gliomas. As used herein, "cancer" refers to all types of cancer or neoplasm or malignant tumours found in mammals, including leukemias, carcinomas, melanomas and sarcomas. Examples of cancers are cancer of the brain, breast, cervix, colon, head and neck, kidney, lung, non-small cell lung, melanoma, mesothelioma, ovary, sarcoma, stomach, uterus and Medulloblastoma.

The term "leukaemia" refers broadly to progressive, malignant diseases of the blood-forming organs and is generally characterized by a distorted proliferation and development of leukocytes and their precursors in the blood and bone marrow. Leukaemia is generally clinically classified on the basis of (1) the duration and character of the disease—acute or chronic, (2) the type of cell involved, myeloid (myelogenous), lymphoid (lymphogenous), or monocytic; and (3) the increase or non-increase in the number of abnormal cells in the blood-leukaemic or aleukaemic (subleukaemic). Leukaemia includes, for example, acute nonlymphocytic leukaemia, chronic lymphocytic leukaemia, acute granulocytic leukaemia, chronic granulocytic leukaemia, acute promyelocytic leukaemia, adult T-cell leukaemia, aleukaemic leukaemia, a leukocythemic leukaemia, basophylic leukaemia, blast cell leukaemia, bovine leukaemia, chronic myelocytic leukaemia, leukaemia cutis, embryonal leukaemia, eosinophilic leukaemia, Gross' leukaemia, hairy-cell leukaemia, hemoblastic leukaemia, hemocytoblastic leukaemia, histiocytic leukaemia, stem cell leukaemia, acute monocytic leukaemia, leukopenic leukaemia, lymphatic leukaemia, lymphoblastic leukaemia, lymphocytic leukaemia, lymphogenous leukaemia, lymphoid leukaemia, lymphosarcoma cell leukaemia, mast cell leukaemia, megakaryocytic leukaemia, micromyeloblastic leukaemia, monocytic leukaemia, myeloblastic leukaemia, myelocytic leukaemia, myeloid granulocytic leukaemia, myelomonocytic leukaemia, Naegeli leukaemia, plasma cell leukaemia, plasmacytic leukaemia, promyelocytic leukaemia, Rieder cell leukaemia, Schilling's leukaemia, stem cell leukaemia, subleukaemic leukaemia, and undifferentiated cell leukaemia.

The term "sarcoma" generally refers to a tumour which is made up of a substance like embryonic connective tissue and is generally composed of closely packed cells embedded in a fibrillar or homogeneous substance. Sarcomas include chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumour sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented haemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumour arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, haematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Additional cancers encompassed by the present invention include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

In one embodiment of the present invention, the oligonucleotide inhibitors are used in the treatment or stabilisation of lung cancer. In another embodiment, the oligonucleotide inhibitors are used in the treatment or stabilisation of colorectal cancer.

ii) Screening Applications

The oligonucleotide inhibitors of the present invention can also be used to inhibit MBD2/dMTase in vitro and in vivo for the purpose of identifying genes that are regulated by MBD2/dMTase and may be important in maintaining the transformed state of a cell. Such genes are potential target genes for anti-cancer therapy and/or diagnosis.

Thus the present invention provides methods of identifying genes which are potential targets for cancer therapy or diagnosis. Such methods involve treatment of a cell with one or more of the MBD2/dMTase oligonucleotide inhibitors of the present invention in order to inhibit expression of MBD2/dMTase followed by comparison of gene expression in the treated cell with that in a suitable control cell. Suitable control cells include, for example, an untreated cell or a cell treated with a control "scrambled" oligonucleotide. In general, the first step in analysis of gene expression is isolation of RNA from the treated and control cells, which can be achieved using standard techniques. Methods of analysing gene expression are well-known in the art and include, for example, Northern blotting techniques, RNase protection assays, differential display, serial analysis of gene expression (SAGE) [see U.S. Pat. No. 6,383,743] and rapid analysis of gene expression (RAGE) [see Wang et al., *Nucl. Acids Res.,* 27:4609-4618 (1999)].

Alternatively, gene expression can be analysed rapidly and conveniently by differential expression analysis using a gene microarray representing a suitable number of genes from the mammal being studied. Microarrays comprise an ordered arrangement of thousands of oligonucleotide probes each representing a separate gene immobilised on a suitable support. Suitable supports for microarrays include, for example, nitrocellulose, plastic, nylon and glass. Typically microarrays useful for this purpose represent between 1,000 and 40,000 genes from the organism of interest. Methods of constructing microarrays are well-known in the art [see, for example, Ausubel, et al., *Current Protocols in Molecular Biology*, John Wiley & Sons, Inc, NY. (1989 and updates)]. In addition, custom-made microarrays are available from many companies. Pre-made microarrays are also commercially available for many organisms including, for example, GeneChip® (Affimetrix, Santa Clara, Calif.), Atlas™ (BD Biosciences-CLONTECH, Palo Alto, Calif.), GEM Microarrays, GeneJet™ array and LifeSeq® (Incyte Genomics, Palo Alto, Calif.), MICROMAX™ Human cDNA Microarray Systems (PerkinElmer Life Sciences, Boston, Mass.) and ResGen™ GeneFilters® (Invitrogen, Huntsville, Ala.).

The RNA isolated from the treated and control cells is hybridized to the microarray under suitable conditions and a routine analysis of the microarray by commercially available scanners and software is conducted to identify genes whose expression is affected (i.e. either induced or suppressed) in the cells treated with the MBD2/dMTase oligonucleotide inhibitors. Suitable hybridization conditions can readily be determined by one skilled in the art using standard techniques. The induced or suppressed genes thus identified are potential target genes for cancer diagnosis and therapy.

Pharmaceutical Compositions

When employed as pharmaceuticals, the oligonucleotide inhibitors are usually administered in the form of pharmaceutical compositions or formulations. Such compositions are prepared in a manner well known in the pharmaceutical art and comprise at least one active compound. In one embodiment of the present invention, the pharmaceutical composition or formulation comprises the oligonucleotide inhibitor. In a related embodiment, the pharmaceutical composition or formulation comprises a vector encoding the oligonucleotide inhibitor.

In accordance with the present invention, the oligonucleotide inhibitors may be incorporated into pharmaceutical compositions in the form of pharmaceutically acceptable salts. The term "pharmaceutically acceptable salt" as used herein refers to salts which retain the biological effectiveness and properties of the oligonucleotide inhibitors of the present invention, and which are not biologically or otherwise undesirable. In many cases, the oligonucleotides are capable of forming acid and/or base addition salts by virtue of the presence of amino and/or carboxyl groups or groups similar thereto.

Pharmaceutically acceptable base addition salts can be prepared from inorganic and organic bases. Salts derived from inorganic bases include, but are not limited to, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Amines in which two or three substituents, together with the amino nitrogen, from a heterocyclic or heteroaryl group are also suitable.

Examples of suitable amines include, but are not limited to, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts can be prepared from inorganic and organic acids. Salts derived from inorganic acids include hydrochloric acid, hydrobromic acid, sulphuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulphonic acid, ethanesulphonic acid, p-toluene-sulphonic acid, salicylic acid, and the like.

Administration of the Oligonucleotide Inhibitors

The oligonucleotide inhibitors of the present invention or pharmaceutical compositions comprising the oligonucleotide inhibitors may be administered in a number of ways depending upon whether local or systemic treatment is desired and upon the area to be treated. Administration may be topical (including ophthalmic and to mucous membranes including vaginal and rectal delivery), pulmonary, e.g. by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g. intrathecal or intraventricular, administration.

The oligonucleotide inhibitors of the present invention may be delivered alone or in combination, and may be delivered along with a pharmaceutically acceptable vehicle. Ideally, such a vehicle would enhance the stability and/or delivery properties. Examples of suitable vehicles include, but are not limited to, liposomes, microparticles or microcapsules. In various embodiments of the invention, the use of such vehicles may be beneficial in achieving sustained release of the active component.

For administration to an individual for the treatment of cancer, the present invention also contemplates the formulation of the oligonucleotide inhibitors or pharmaceutical compositions comprising the oligonucleotide inhibitors into oral dosage forms such as tablets, capsules and the like. For this purpose, the oligonucleotide inhibitors or pharmaceutical compositions comprising the oligonucleotide inhibitors can be combined with conventional carriers, such as magnesium carbonate, magnesium stearate, talc, sugar, lactose, pectin, dextrin, starch, gelatine, tragacanth, methylcellulose, sodium carboxymethyl-cellulose, low melting wax, cocoa butter and the like. Diluents, flavouring agents, solubilizers, lubricants, suspending agents, binders, tablet-disintegrating agents and the like can also be employed, if required. The oligonucleotide inhibitors or pharmaceutical compositions comprising the oligonucleotide inhibitors can be encapsulated with or without other carriers. In all cases, the proportion of active ingredients in any solid and liquid composition will be at least sufficient to impart the desired activity to the individual being treated upon oral administration. The present invention further contemplates parenteral injection of the oligonucleotide inhibitors or pharmaceutical compositions comprising the oligonucleotide inhibitors, in which case they are used in the form of a sterile solution containing other solutes, for example, enough saline or glucose to make the solution isotonic.

For administration by inhalation or insufflation, the oligonucleotide inhibitors or pharmaceutical compositions comprising the oligonucleotide inhibitors can be formulated into an aqueous or partially aqueous solution, which can then be utilized in the form of an aerosol. The present invention also contemplates topical use of the oligonucleotide inhibitors or pharmaceutical compositions comprising the oligonucleotide inhibitors. For this purpose they can be formulated as dusting powders, creams or lotions in pharmaceutically acceptable vehicles, which are applied to affected portions of the skin. Alternatively, the oligonucleotide inhibitors can be formulated as transdermal delivery devices ("patches"). Such transdermal patches can be used to provide continuous or discontinuous infusion of the oligonucleotide inhibitors in controlled amounts. The construction and use of transdermal patches for the delivery of pharmaceutical agents is well-known in the art [see, for example, U.S. Pat. No. 5,023,252]. Such patches may be constructed for continuous, pulsatile, or "on demand" delivery of pharmaceutical agents.

The present invention also provides for administration of the oligonucleotide inhibitors in the form of genetic vector constructs that are designed to direct the in vivo synthesis of the oligonucleotide inhibitors. Within the vector construct, the nucleic acid sequence encoding the oligonucleotide inhibitor is under the control of a suitable promoter. The vector construct may additionally contain other regulatory control elements known in the art. Methods of constructing and administering such genetic vector constructs for in vivo synthesis of oligonucleotide inhibitors, such as antisense oligonucleotides, are well-known in the art. For example, U.S. Pat. No. 6,265,167 teaches an efficient method for the introduction, expression and accumulation of antisense oligonucleotides in the cell nucleus. This method allows the antisense oligonucleotide to hybridize to the sense mRNA in the nucleus, and thereby prevents the antisense oligonucleotide being either processed or transported into the cytoplasm.

An alternative method of delivery involves "shotgun" delivery of the naked oligonucleotides across the dermal layer or directly into a region to be treated. The delivery of "naked" oligonucleotides by direct injection is well-known in the art [see, for example, U.S. Pat. No. 5,580,859]. In addition, methods of delivering oligonucleotides to a subject by coating them onto particles and accelerating the coated particles into the cells of a subject is also known in the art [see, for example, U.S. Pat. Nos. 5,865,796 and 5,922,685]. It is contemplated that the oligonucleotide inhibitors may be packaged in a lipid vesicle or otherwise associated with lipids prior "shotgun" delivery to the subject.

The dosage requirements for the oligonucleotide inhibitors of the present invention vary with the particular compositions employed, the route of administration, the severity of the symptoms presented and the particular subject being treated. Dosage requirements can be determined by standard clinical techniques, known to a worker skilled in the art. Treatment will generally be initiated with small dosages less than the optimum dose of the compound. Thereafter the dosage is increased until the optimum effect under the circumstances is reached. In general, the oligonucleotide inhibitors are administered at a concentration that will generally afford effective results without causing any harmful or deleterious side effects. Administration can be either as a single unit dose or, if desired, the dosage can be divided into convenient subunits that are administered at suitable times throughout the day.

Kits i) Therapeutic

The present invention additionally provides for therapeutic kits containing one or more oligonucleotide inhibitors, or one or more expression vectors encoding the oligonucleotide inhibitors, in pharmaceutical compositions for use in the treatment of cancer. The kits may further comprise one or more other anti-cancer therapeutics for use in combination with the oligonucleotide inhibitor(s). Individual components of the kit would be packaged in separate containers and, associated with such containers, can be a notice in the form prescribed by a governmental agency regulating the manufacture, use or sale of pharmaceuticals or biological products, which notice reflects approval by the agency.

When the components of the kits according to the present invention are provided in one or more liquid solutions, the liquid solution can be an aqueous solution, for example a sterile aqueous solution. For in vivo use, the oligonucleotide inhibitor may be formulated into a pharmaceutically acceptable composition. In this case the container means may itself be an inhalant, syringe, pipette, eye dropper, or other such like apparatus, from which the formulation may be applied to an infected area of the subject, such as the lungs, injected into an subject, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. Irrespective of the number or type of containers, the kits of the invention also may comprise, or be packaged with, an instrument for assisting with the injection/administration or placement of the ultimate complex composition within the body of the subject. Suck an instrument may be an inhalant, syringe, pipette, forceps, measured spoon, eye dropper or any such medically approved delivery vehicle.

ii) Screening

The oligonucleotide inhibitors according to the present invention can form part of a kit for screening for genes whose expression is affected by an MBD2/dMTase and which are potential target genes for cancer therapy and/or diagnosis. Such kits comprise one or more MBD2/dMTase oligonucleotide inhibitors. One or more of the oligonucleotides provided in the kit can incorporate a detectable label, or the kit may include reagents for labeling the oligonucleotides. The kits can optionally include reagents for the isolation of RNA, reagents for the synthesis of cDNA, and/or reaction vessels. One or more of the components of the kit may be lyophilised and the kit may further comprise reagents suitable for the reconstitution of the lyophilised components. The kit can additionally contain instructions for use.

To gain a better understanding of the invention described herein, the following examples are set forth. It should be understood that these examples are for illustrative purposes only. Therefore, they should not limit the scope of this invention in any way.

EXAMPLES

Oligonucleotide Sequences—Antisense DNA oligonucleotides were designed to hybridize to human MBD2 cDNAs (A1 and A2 to that described in Bhattacharya, S. K., Ramchandani, S., Cervoni, N., and Szyf, M. (1999) *Nature* 397, 579-583 and A3-A10 to that described in Hendrich, B., and Bird, A. (1998) *Mol Cell Biol* 18, 6538-6547). The sequences as follows:

| A1, | 5'GGCAATCCATCCTCTTCC3' | [SEQ ID NO: 5] |
| A2, | 5'CTTCCTCCTTCTTCCATC3' | [SEQ ID NO: 6] |
| A3, | 5'CAACAGTATTTCCCAGGT3' | [SEQ ID NO: 7] |
| A4, | 5'TGTAGCCTCTTCTCCCAG3' | [SEQ ID NO: 8] |
| A5, | 5'ATCCAGCCCCCTCCCCAG3' | [SEQ ID NO: 9] |
| A6, | 5'CACTCTCCCCCTCCCCCT3' | [SEQ ID NO: 10] |
| A7, | 5'TCAACAGTATTTCCCAGGTA3' | [SEQ ID NO: 11] |
| A10, | 5'UCAACAGTATTTCCCAGGUA3' | [SEQ ID NO: 12] |
| A11, | 5'AUGGACCCTTTATGACAACU3' | [SEQ ID NO: 13] |
| 1582, | 5'CGATTCAATCCTCACCTCTC3'. | [SEQ ID NO: 14] |

Antisense oligonucleotides A1-A5 have a phosphorothioate (PS) backbone; A7 has a mixed phosphodiester and PS backbone, A7 also contains an inverted thymine base at the 3' end. The antisense oligonucleotide A10 is a modification of oligonucleotide A7 in which a 2' O-methyl modification has been positioned on the ribose of the first and last 4 nucleotides. Control oligonucleotide A11 is the reverse sequences of A10, with oligonucleotide 1582 used as a nonspecific control for the rest of the experiments.

Oligos were selected to avoid dimers and stem loop structures as well as CpG dinucleotides (Ballas, Z. K., Krieg, A. M., Warren, T., Rasmussen, W., Davis, H. L., Waldschmidt, M., and Weiner, G. J. (2001) *J Immunol* 167, 4878-4886). A4-A10 included the TCCC tetranucleotide motif. After synthesis, oligonucleotides were cleared of contaminants by desalting and gel purification (A1-A6), HPLC (A7), and ion exchange HPLC (A10, A11). Oligonucleotide synthesis was performed by OligosEtc (A1-A7, Wilsonville, Oreg.) and Integrated DNA Technologies (A10, A11 Coralville Iowa).

Example 1

Inhibition of mbd2/dMTase mRNA Expression by Antisense Oligonucleotides

A. To screen and test antisense inhibitors of MBD2/dMTase, the human non-small cell lung carcinoma cell line A549 (ATCC# CCL-185), which expresses high levels of MBD2/dMTase, was treated with 200 nM of either the selected antisense oligonucleotide or a scrambled control. Lipofectin (6.25 µg/ml) was used as the lipid carrier. The cells were treated twice (0 and 24 h) and harvested 48 h post treatment (see protocol in B).

Figure 4:
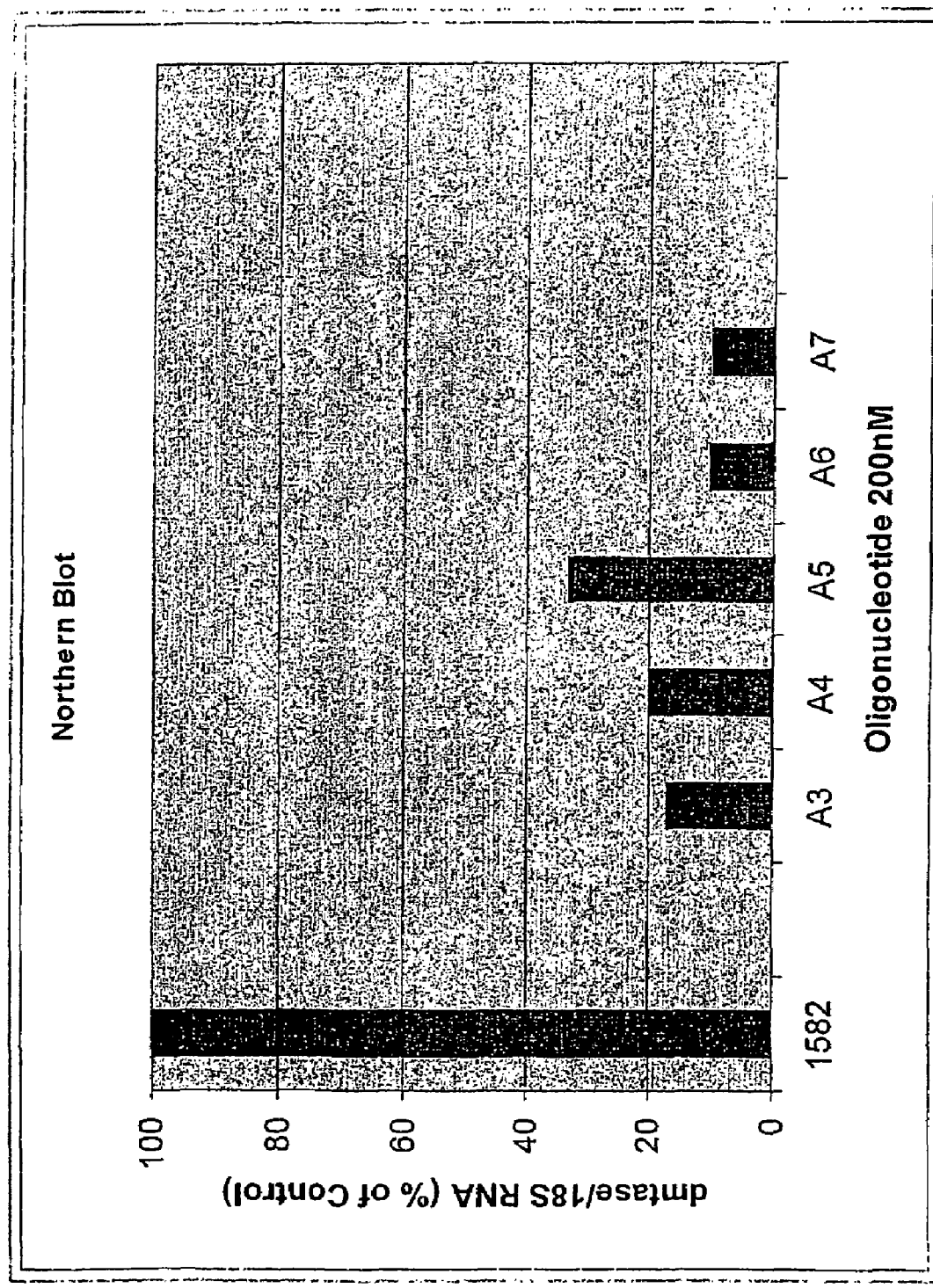
FIG. 4 illustrates the inhibition of MBD2/dMTase mRNA expression in non-small cell lung carcinoma cells after treatment with antisense oligonucleotide A3, A4, A5, A6 or A7, or with scrambled control oligonucleotide 1582 [SEQ ID NO: 14].

To determine whether the treatment with the antisense compound results in reduction of MBD2/dMTase levels, total mRNA was isolated from the cells and used to perform a Northern blot analysis. A $^{32}$P-labeled cDNA probe was used for hybridization. The signal obtained with the specific probe was normalized to total RNA in the lane as determined by hybridization with an 18S rRNA-specific oligonucleotide probe (see protocol in B). The results for antisense oligonucleotides A3, A4, A5, A6 and A7 are shown in FIG. 4, together with data for the scrambled control oligonucleotide 1582.

B. A549 non-small cell human lung carcinoma cells (ATCC# CCL-185), HCT116 human colon carcinoma cells (ATCC# CCL-247), MRHF human foreskin fibroblasts (Biowhittaker, Wakersville, Md.) were cultured free of antibiotics in the recommended media to facilitate oligo transfection and plated at a density of $3 \times 10^5$ per 10 cm plate 24 to 48 hours before transfection. Antisense oligonucleotides were added to cells at a final concentration of 20, 50 or 200 nM using either 6.25 µl/ml Lipofectin for A549 cells or 4 µl/ml Lipofectamine (Invitrogen, Carlsbad Calif.) for HCT116 cells as lipid carriers. Transfection was repeated after 24 hours, cells were harvested with TRIzol (Invitrogen), total RNA was prepared according to manufacturer's recommendation and was subjected to gel electrophoresis, Northern blot transfer onto Hybond-N+ membrane (Amersham pharmacia biotech) according to the manufacturer's recommendations and hybridization with a 1.3 kb MBD2b cDNA probe (Bhattacharya, S. K., Ramchandani, S., Cervoni, N., and Szyf, M. (1999) *Nature* 397, 579-583) in a 10 ml hybridization solution containing 7% SDS, 0.5 M sodium phosphate pH 6.8, and 1 nM EDTA at 68° C. for 4 hours. Following washing and exposure to a phosphor-imaging plate, the membrane was stripped and hybridized to a $^{32}$P-labeled 18S rRNA probe as previously described (Szyf, M., Tanigawa, G., and McCarthy, P. L., Jr. (1990) *Mol Cell Biol* 10, 4396-4400). The signals for MBD2 and 18S were quantified by densitometry and the intensity of the MBD2 signal was normalized to the signal obtained for 18S. A549 cells were harvested after a single treatment with oligo, nuclear extracts prepared as previously described (Szyf, M., Bozovic, V., and Tanigawa, G. (1991) *J Biol Chem* 266, 10027-10030) were resolved by electrophoresis, and membranes were probed with 1:200 dilution of a monoclonal anti-MBD2 antibody (#147, Imgenex, San Diego, Calif.) in 0.05M Tris-0.2M NaCl 0.5% Tween 20 pH 7.6 solution overnight at 4° C. The blot was then reacted with a secondary anti-mouse monoclonal antibody at a 1:20,000 dilution and the band developed with the ECL kit from Amersham pharmacia biotech. The Western blot membrane was then stained with BLOT FastStain from CHEMICON International according to the manufacturer's recommendations to verify equal loading and transfer of the proteins onto the membranes.

Figure 17:
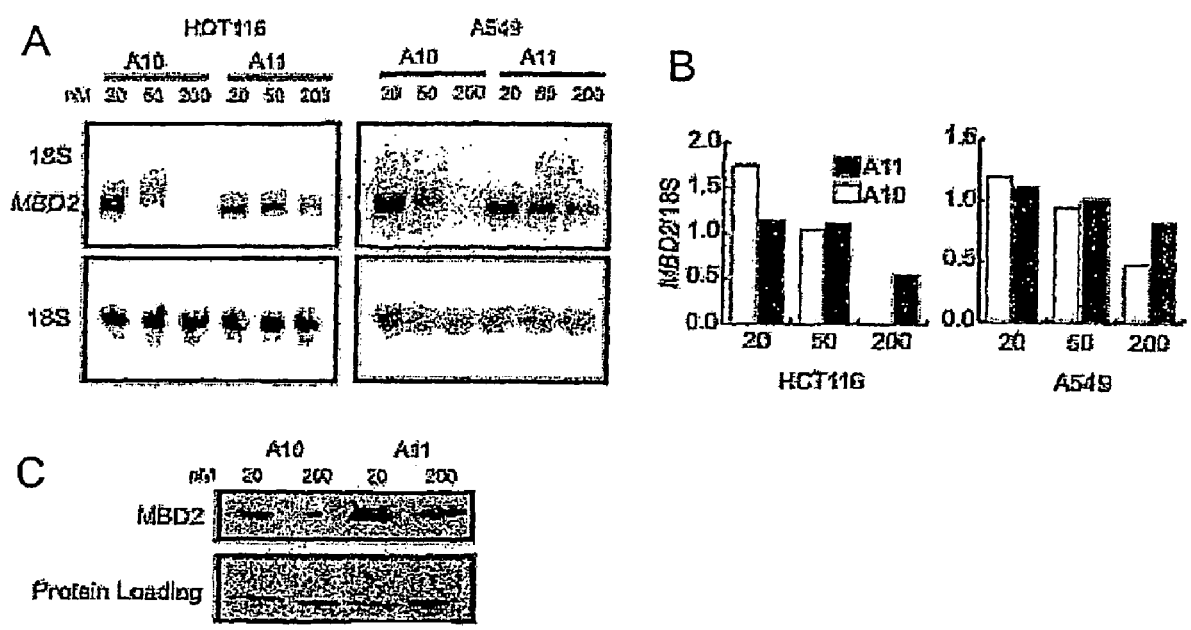
FIG. 17 (A) presents representative Northern blots measuring MBD2/dMTase expression in A549 and HCT116 cells following treatment with antisense oligonucleotide A10 or control oligonucleotide A11 and quantification of these blots (B). (C) presents Western blots of nuclear extracts from A10 antisense versus A11 control treated A549 cells. Nonspecific protein staining shown below as a measure of equal protein loading.

Specific and dose-dependent inhibition of target MBD2 mRNA was observed in both A549 and HCT116 cells treated with A10 (FIGS. 17A and B) in comparison with the A11 control. Concomitant with a reduction of MBD2 mRNA, reduction of protein was also observed in antisense but not control treated A549 cells (FIG. 17C).

Example 2

Figure 5:
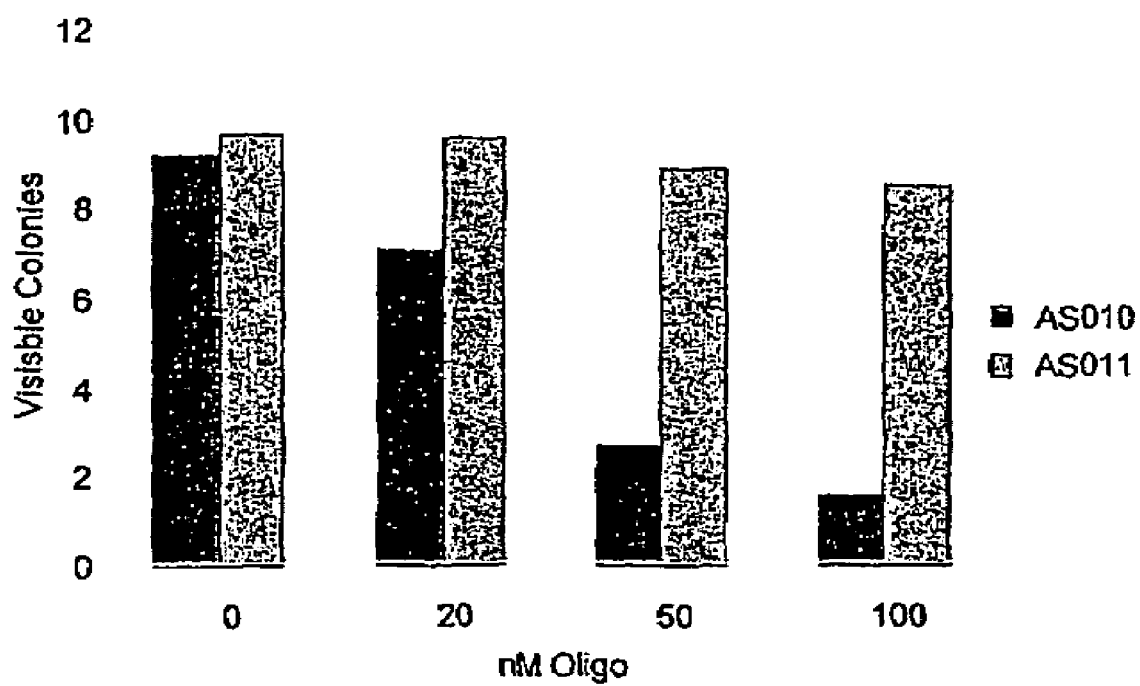
FIG. 5 presents the results of treatment of human non-small lung cancer cells (cell-line A549) with increasing concentrations of MBD2/dMTase antisense oligonucleotides A10 and the reverse scrambled control A11 [SEQ ID NO: 13].

Inhibition of Anchorage-Independent Growth of Cancer Cells by Antisense Oligonucleotides to mbd2/dMTase A human non-small cell lung carcinoma cell line A549, which expresses high levels of MBD2/dMTase, was treated with increasing concentrations of either the selected antisense oligonucleotide A10 or a reverse scrambled control oligonucleotide A11 for 48 h. An equal number of live cells were plated onto 0.33% agar with enriched medium. Colonies growing in an anchorage independent manner were counted by visual examination 3 weeks after plating to determine the anti-tumourigenic activity of the compounds. Anchorage-independent growth is an indicator of tumourigenicity. Results are shown in FIG. 5.

Figure 6:
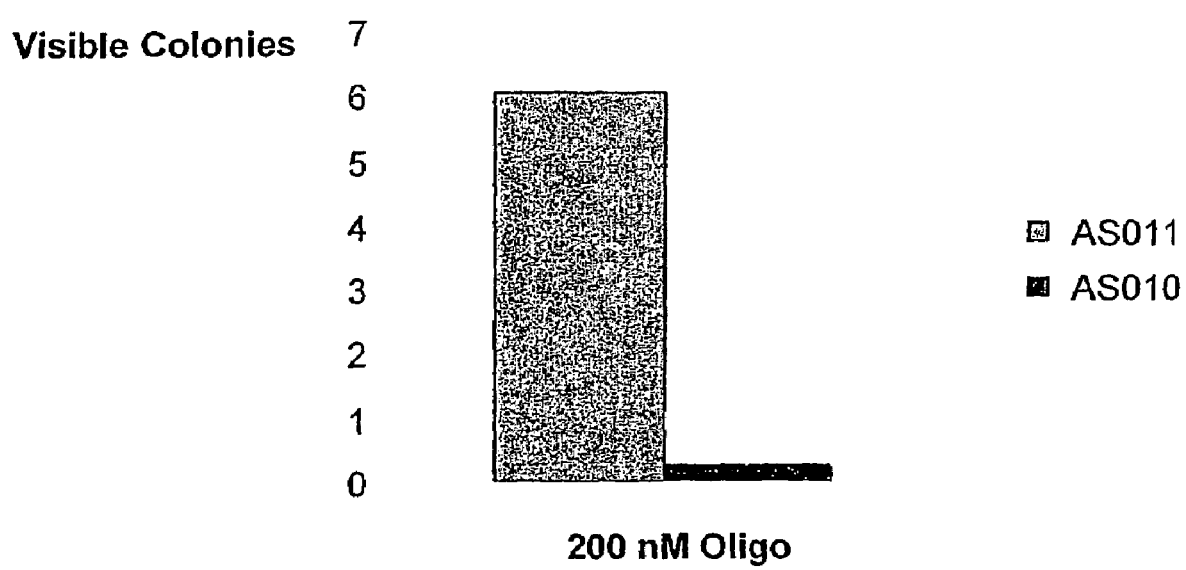
FIG. 6 presents the results of treatment of human colorectal carcinoma cells (cell-line HCT116) with either the MBD2/dMTase antisense oligonucleotide A10 or the reverse scrambled control A11.

Similar experiments were conducted using the human colorectal carcinoma cell line HCT116. Cells were treated with either 200 nM of the MBD2/dMTase antisense oligonucleotide A10 or the reverse scrambled control A11 for 48 h and were then plated onto soft agar. Colonies growing in an anchorage-independent manner were scored after 3 weeks. The results are shown in FIG. 6 and indicate that the antisense oligonucleotide A10 effectively inhibits the anchorage-independent growth of HCT116 colorectal carcinoma Detailed experimental protocols for the above experiments are provided below:

To determine anchorage-independent growth on soft agar, 3000 live cells treated with a single dose of antisense or control oligos for 24 hours were seeded into soft agar and plated in triplicate in a six well plate for 21 days as previously described (Slack, A., Cervoni, N., Pinard, M., and Szyf, M. (1999) *J Biol Chem* 274, 10105-10112). The number of colonies (>10 cells per colony) in five random fields (40×) per well, throughout all planes of the triplicate wells, was counted after 21 days under microscopy.

Example 3

In Vitro Toxicity Tests

Figure 16:
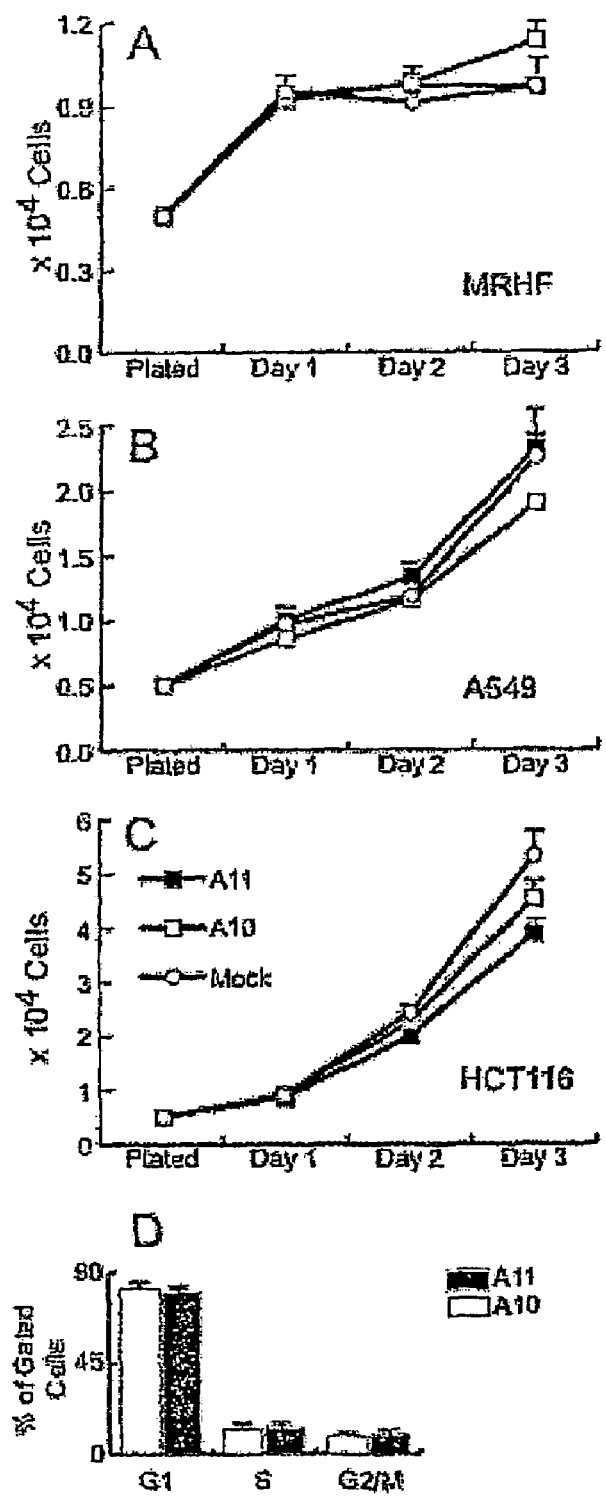
FIG. 16 depicts the growth curves of MRHF (A), A549 (B), and HCT116 (C) following treatment with A10 (open squares) or A11 (solid squares), or mock transfection (open circles) (averages of three replicates +SEM). (D) demonstrates that antisense oligonucleotide A10 has no effect on cell cycle progression of A549 cells; error bars are SEM for triplicate transfections.

For anchorage-dependent cell growth experiments, A549, HCT116, and MRHF cells were plated at the concentration of 50,000 cells/dish. After 24 hours, cells were treated with 200 nM of control oligonucleotide A11 or antisense oligonucleotide A10. Treatments were repeated after 24 h and cells were harvested 24, 48 and 72 h after the second treatment (Day 1, Day 2, Day 3, respectively). Cell viability was measured by trypan blue exclusion. Results are shown in FIG. 16A-C.

To determine cell cycle kinetics, the cells were fixed for 18 h in 70% ethanol at 4° C., and treated with propidium iodide to label DNA (Vindelov, L. L., and Christensen, I. J. (1988) *Eur J Haematol Suppl* 48, 69-76). Twenty thousand cells were sorted in triplicate for DNA content in a Becton Dickinson (Franklin Lakes, N.J.) FACScan cell sorter and data were acquired by the LYSIS II program Results are shown in FIG. 16D and indicate that antisense oligonucleotide A10 does not affect cell cycle progression.

Example 4

Inhibition of Tumour Growth by Ex Vivo Treatment of Carcinoma Cells with Antisense Oligonucleotide Inhibitors of MBD2/dMTase Male CD1 nude mice were obtained from Charles River Laboratories and used when 8-10 weeks old. Experimental procedures were carried out according to the regulations of the Canadian Council on Animal Care and under protocols reviewed and accepted by the McGill University Animal Care Committee.

Figure 7:
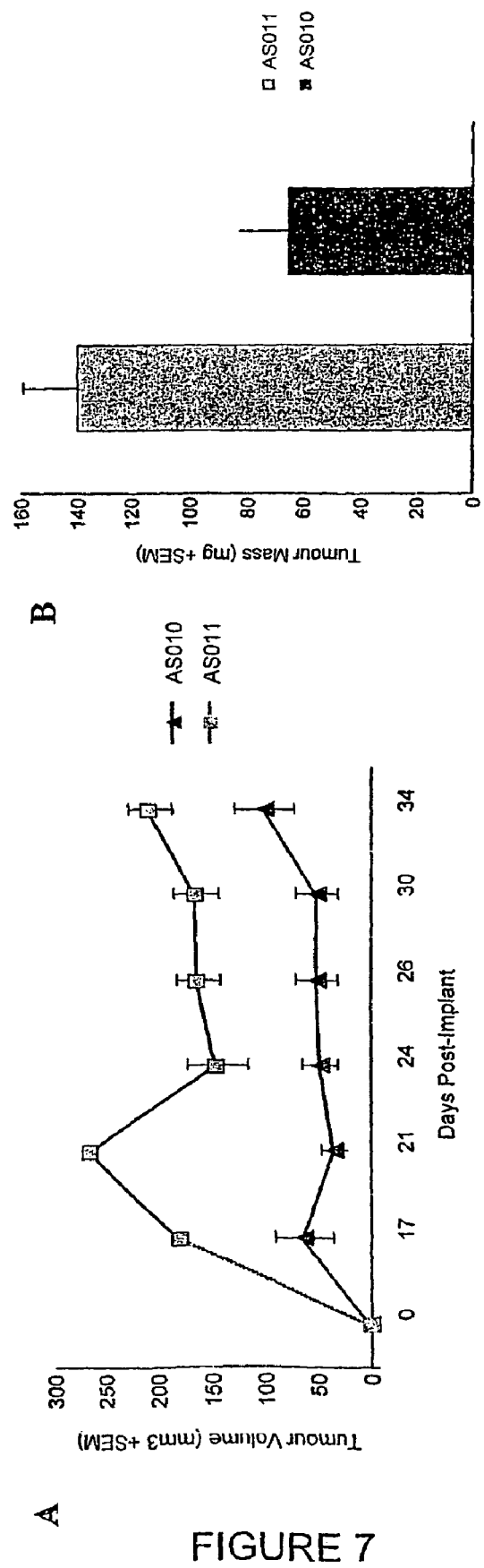
FIG. 7 (A) illustrates the change in tumour volume and (B) demonstrates the relative tumour mass of in vivo xenografts of the human non-small lung cancer cell-line A549 in nude mice. The cell-line was treated in vitro with either antisense oligonucleotide A10 or control scrambled oligonucleotide A11 prior to transplantation.

A. Human lung carcinoma cells (A549 cell-line) were treated with either 200 nM of the MBD2/dMTase antisense oligonucleotide A10 or the control oligonucleotide A11 for 24 h. An equal number of live cells was implanted in nude mice and tumour volume was monitored every two days. After 34 days the animals were sacrificed and the tumours were weighed. The results are shown in FIGS. 7A and 7B and demonstrate that tumours derived from cells that were treated once for 24 h with MBD2/dMTase antisense oligonucleotide A10 had significantly lower weights than those derived from cells treated with the control oligonucleotide.

Figure 8:
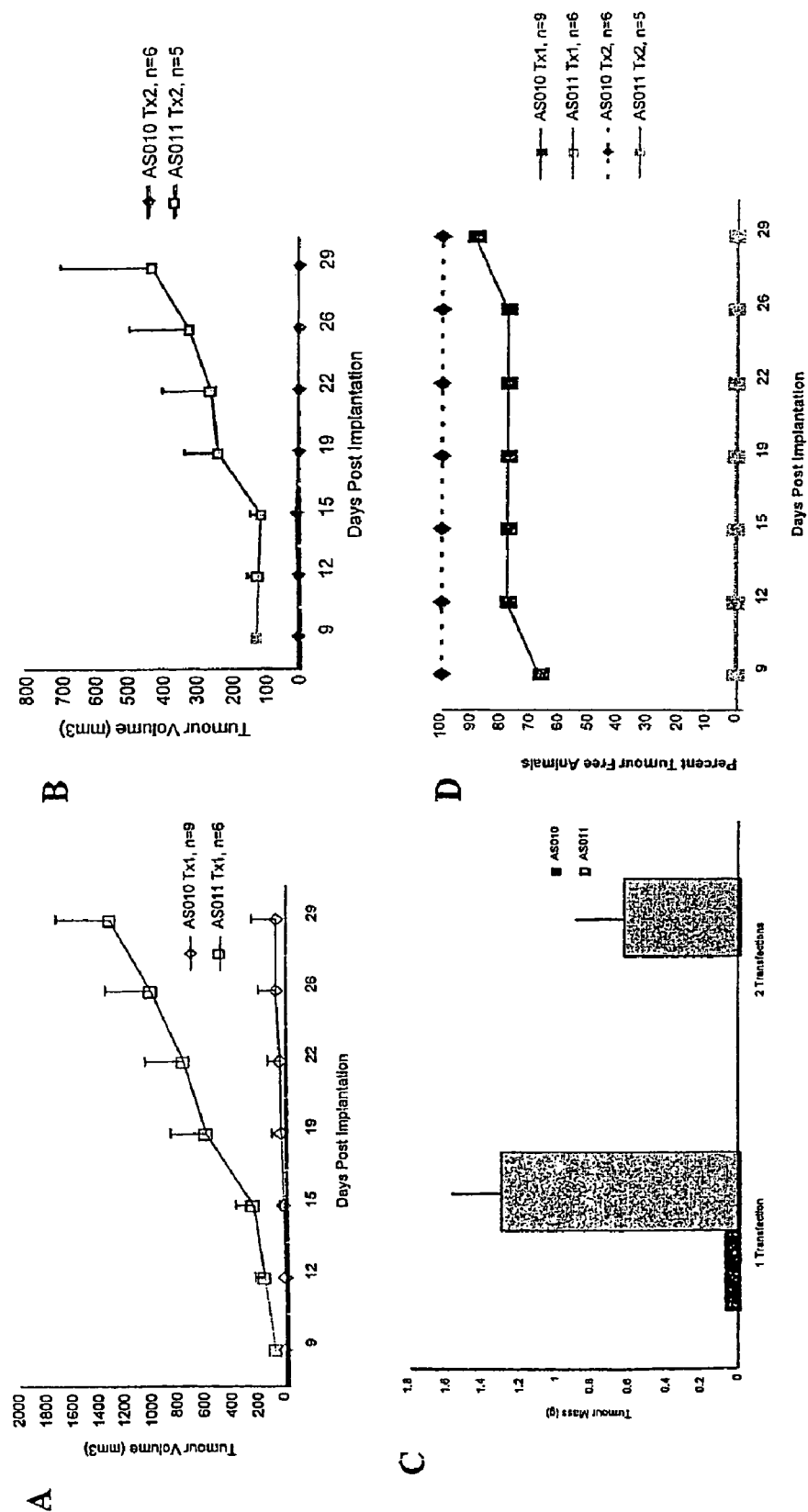
FIG. 8 illustrates (A) the change in tumour volume for a single treatment group (B) the change in tumour volume for a double treatment group, (C) the relative tumour mass and (D) the number of tumour-free animals per treatment for nude mice carrying in vivo xenografts of the human colorectal carcinoma cell-line HCT116. The cell-line was treated in vitro with either antisense oligonucleotide A10 or control scrambled oligonucleotide A11 prior to implantation.

B. Human colorectal carcinoma cells (HCT116 cell-line) were treated in vitro with 200 nM of either MBD2/dMTase antisense oligonucleotide A10 or the control oligonucleotide A11 for either 24 h (single treatment) or 48 h (double treatment). An equal number of live cells ($10^6$) were implanted into nude mice (n per group=10). Tumour volumes were measured and graphed. FIG. 8A shows the results for the single treatment and FIG. 8B shows the results for the double treatment. The tumours were harvested and weighed after 28 days and the results are shown in FIG. 8C. The number of tumour-free animals per treatment are shown in FIG. 8D. The results indicate that MBD2/dMTase antisense treatment effectively inhibited the ability of HCT116 colorectal carcinoma cells to grow as tumours in a nude mouse xenograft model.

Example 5

Inhibition of Tumour Cell Growth In Vivo by Oligonucleotide Inhibitors of MBD2/dMTase Male CD1 nude mice were obtained from Charles River Laboratories and used when 8-10 weeks old. Experimental procedures were carried out according to the regulations of the Canadian Council on Animal Care and under protocols reviewed and accepted by the McGill University Animal Care Committee.

Tumour cells ($2.5 \times 10^6$) from the human non-small cell lung carcinoma cell line A549, were injected subcutaneously in the flank of the animals on day 0. Antisense treatment was initiated 3 days post-implantation. Antisense oligonucleotide A10 or scrambled control oligonucleotide A11 were administered intravenously by bolus injection into the tail vein 3 times per week for 30 days at dosages of 2 mg/kg, 4 mg/kg or 8 mg/kg (n=8 per treatment group). Tumour volumes are monitored every 2 days.

Figure 9:
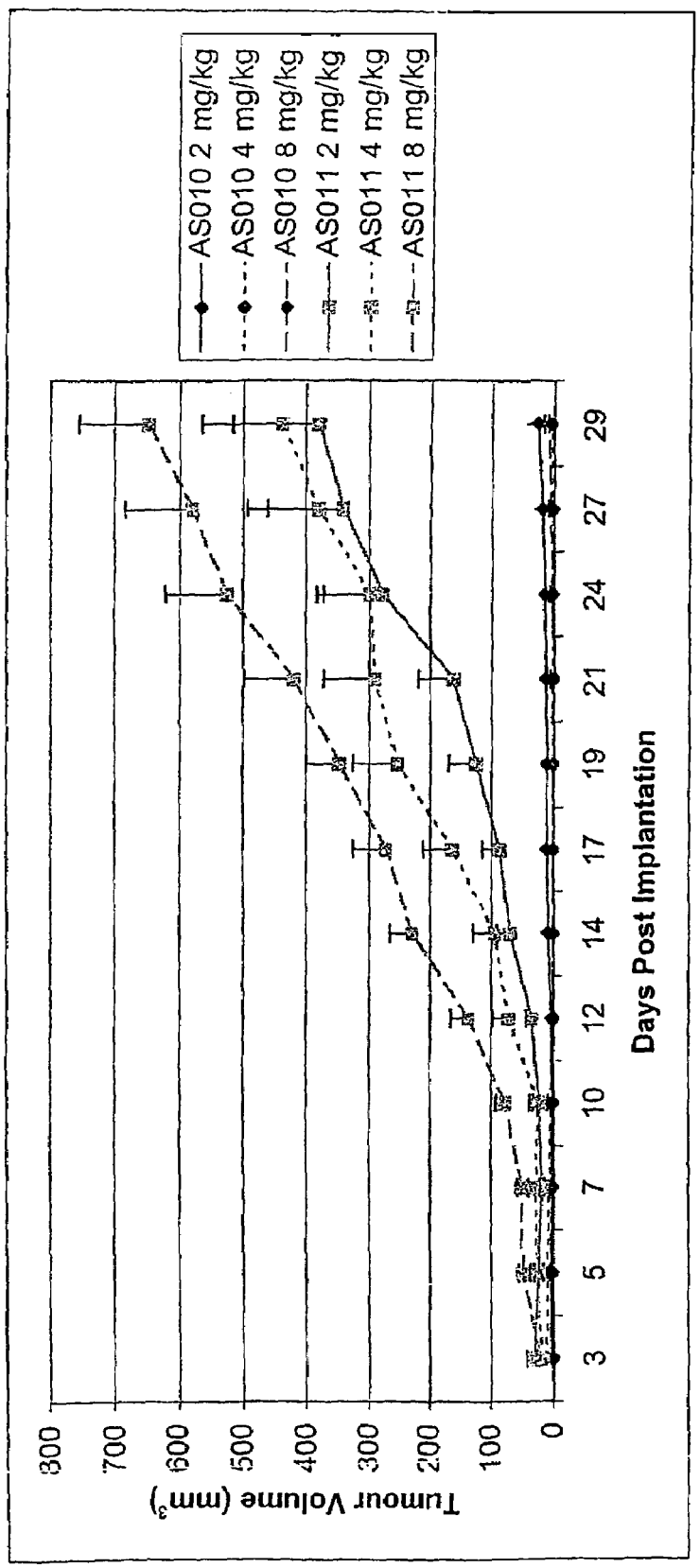
FIG. 9 presents the results of treatment of in vivo xenografts of the human non-small lung cancer cell-line A549 in nude mice with varying concentrations of either antisense oligonucleotide A10 or control scrambled oligonucleotide A11.
Figure 10:
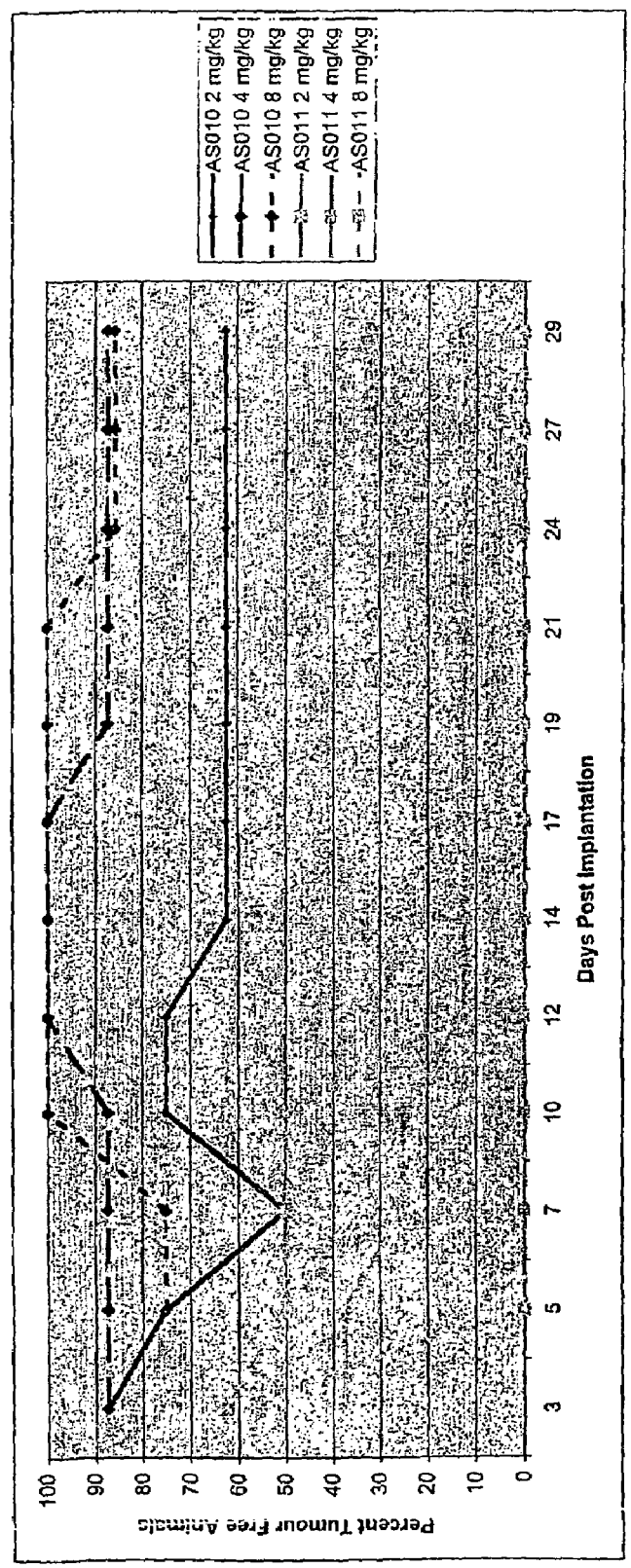
FIG. 10 depicts the increase in percentage of tumour-free animals following treatment of in vivo xenografts of the human non-small lung cancer cell-line A549 in nude mice with antisense oligonucleotide A10.
Figure 11:
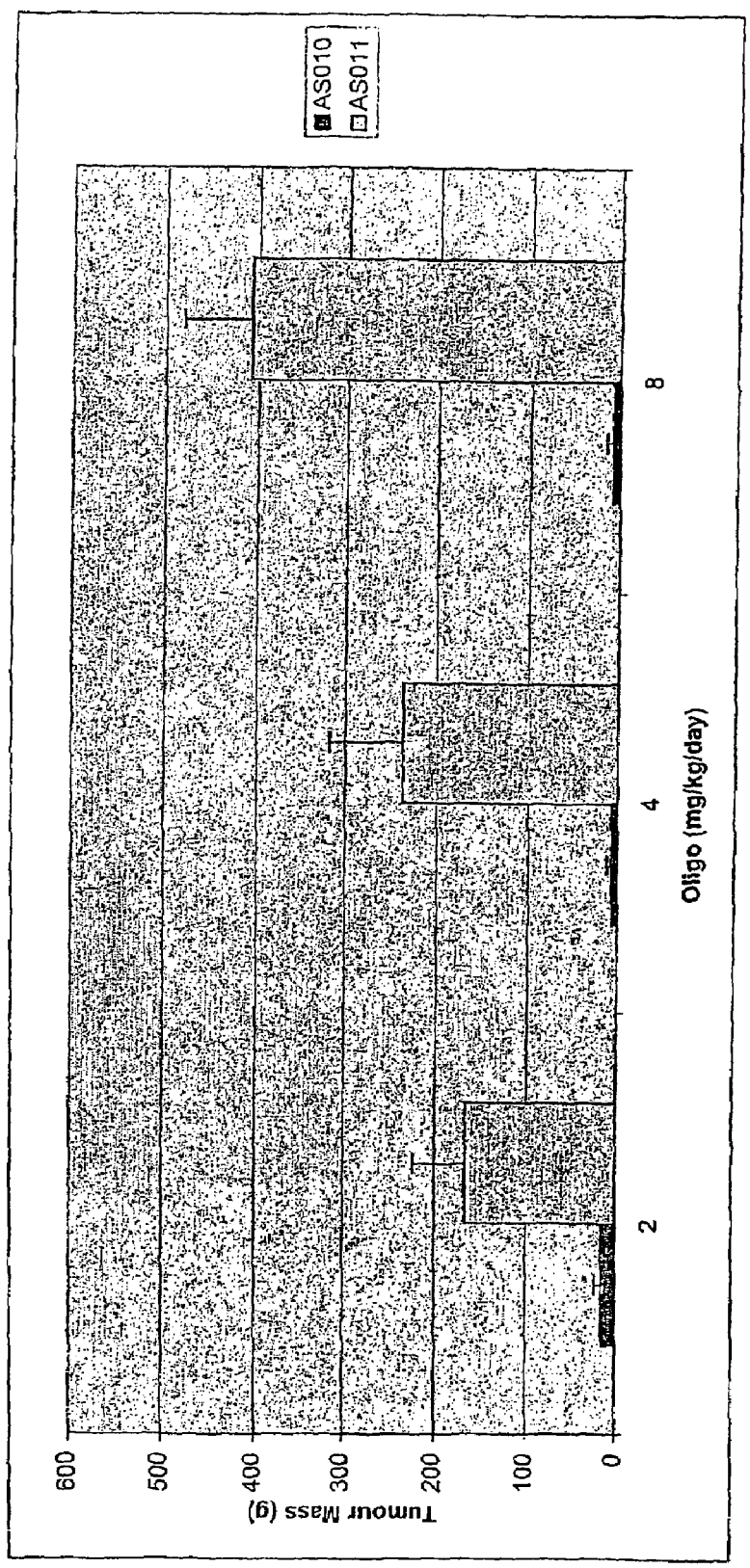
FIG. 11 depicts the decrease in tumour weight following treatment of in vivo xenografts of the human non-small lung cancer cell-line A549 in nude mice with antisense oligonucleotide A10.
Figure 12:
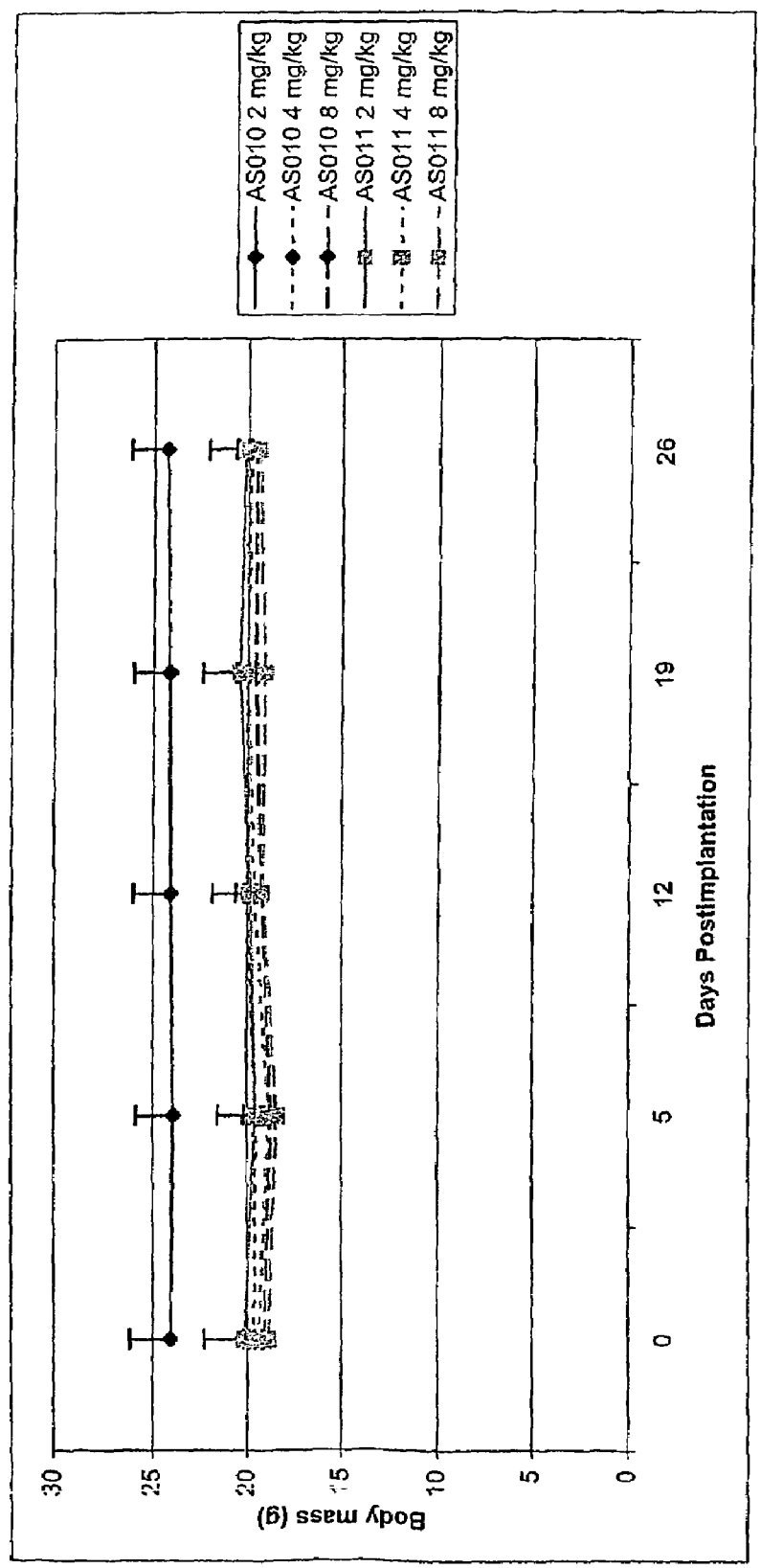
FIG. 12 demonstrates that antisense oligonucleotide A10 does not cause overt toxicity in nude mice.
Figure 13:
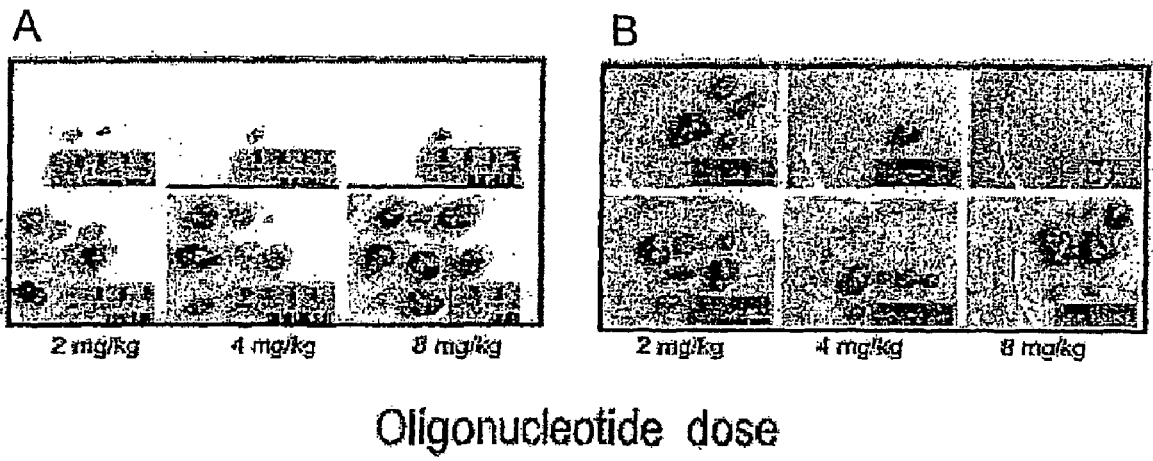
FIG. 13 depicts the reduction in tumour size following treatment of in vivo xenografts of (A) the human non-small lung cancer cell-line A549, and (B) the human colorectal carcinoma cell-line HCT116, in nude mice with antisense oligonucleotide A10.

Tumour volumes are measured throughout the experiment to monitor the progress of tumour growth and the results are shown in FIG. 9. The number of tumour-free animals was also assessed and the results are shown in FIG. 10. The general toxic effect of antisense oligonucleotide A10 and control oligonucleotide A11 was evaluated by measuring the effect on animal body weight as shown in FIG. 12. Following sacrifice of the animals at day 30, the tumours were harvested and weighed. The average weights and relative sizes of the excised tumours are shown in FIGS. 11 and 13, respectively. A significant decrease was observed in the weight and size of those tumours harvested from the mice treated with antisense oligonucleotide A10 relative to those harvested from mice treated with the control oligonucleotide.

Example 6

Inhibition of Tumour Cell Growth In Vivo by Oligonucleotide Inhibitors of MBD2/dMTase #2

Figure 14:
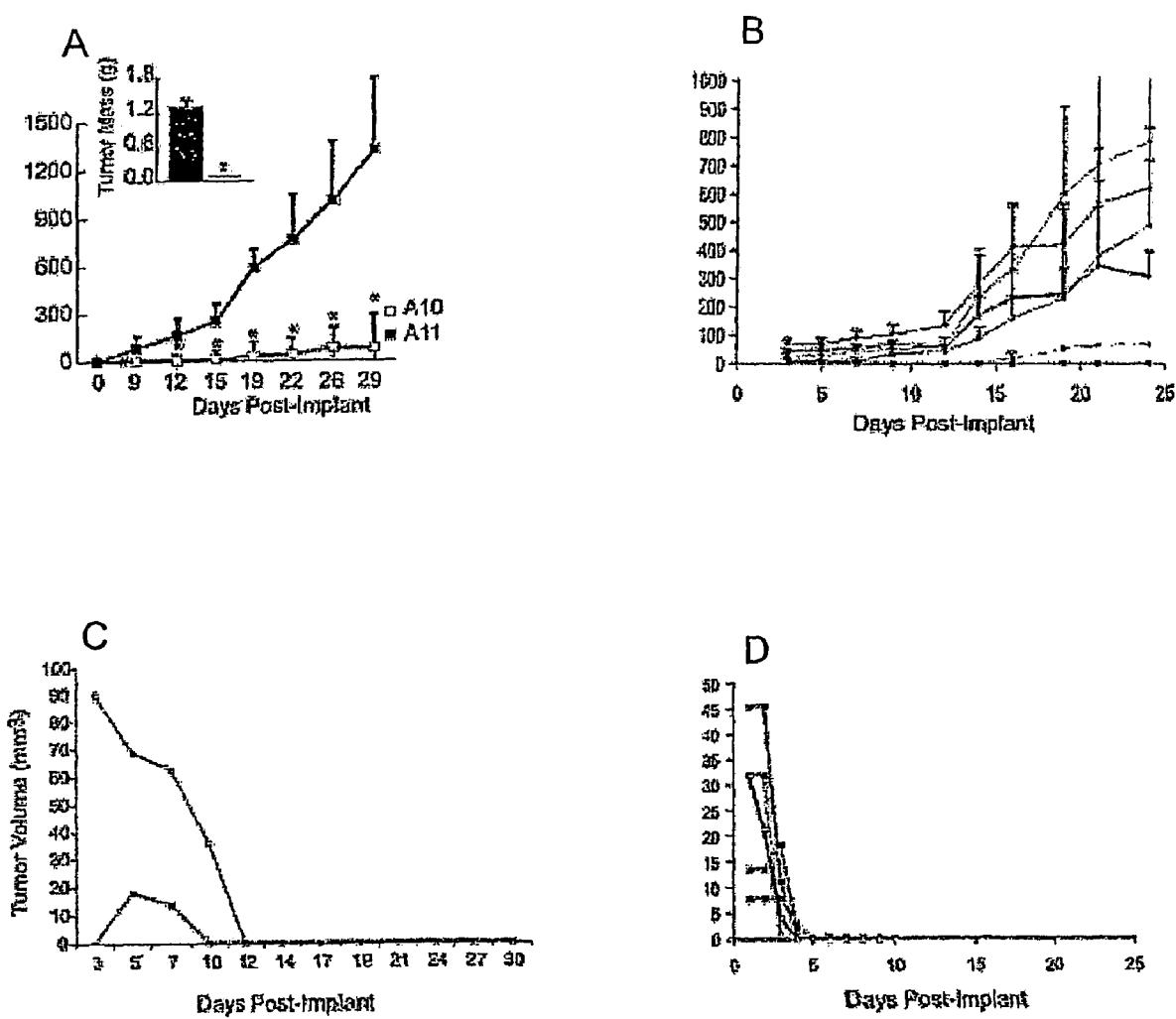
FIG. 14 (A) depicts the inhibition of in vivo xenografts of the human colorectal carcinoma cell-line HCT116 after in vitro treatment with either antisense oligonucleotide A10 or control scrambled oligonucleotide A11 prior to implantation. Graph shows average tumour volume and mass (in inset) +/−SEM. Stars above the bars indicate statistical significance of $p<0.05$ (two-sided student t-test). (B) shows inhibition of growth of naïve HCT116 cells implanted into nude mice by antisense oligonucleotide A10 in a dose-dependent fashion. (C) and (D) show complete tumour regression in mice with xenografts of A549 and HT116 cells, respectively, following treatment with antisense oligonucleotide A10.

$2.5 \times 10^6$ naïve A549 or HCT116 cells were injected subcutaneously into BALB/cAnNCrl-nuBR nude mice. Three days post implantation, when solid tumours were already visible, the mice (8 per group) were injected via tail vein 3 times per week with control oligonucleotide A11 or antisense oligonucleotide A10, at doses of 2, 4, or 8 mg/kg dissolved in 100 µl sterile PBS. The mice were monitored for tumour growth 3 times per week, and tumor volume was estimated by using $V=(L \times W^2) \times 0.5$, where L is the length and W is the width of a xenograft (Bandyopadhyay, A., Lopez-Casillas, F., Malik, S. N., Montiel, J. L., Mendoza, V., Yang, J., and Sun, L. Z. (2002) *Cancer Res* 62, 4690-4695) and observed for cachexia, lethargy, lesions and other signs of toxicity. The mice were sacrificed after 24 or 29 d by exsanguination and their blood was analyzed for liver and kidney function as well as hemocyotology. A549 cells were more sensitive to systemic antisense treatment than in vitro treatment. All 3 doses of A10 showed significant inhibitory effects on tumour growth, with complete tumour regression seen in 2 mice dosed with 8 mg/kg (FIG. 14C). One mouse in this same antisense group died after 17 days postimplantation but the cause of death is unclear. Numbers of tumour-free mice for 2, 4, and 8 mg/kg groups were 5/8, 7/8, 7/8 for A10, and 1/8, 1/8 and 0/8 for A11 treatments. Thus, MBD2 antisense treatment essentially eliminated the ability of A549 cells to grow as tumour xenoplants in nude mice.

Figure 15:
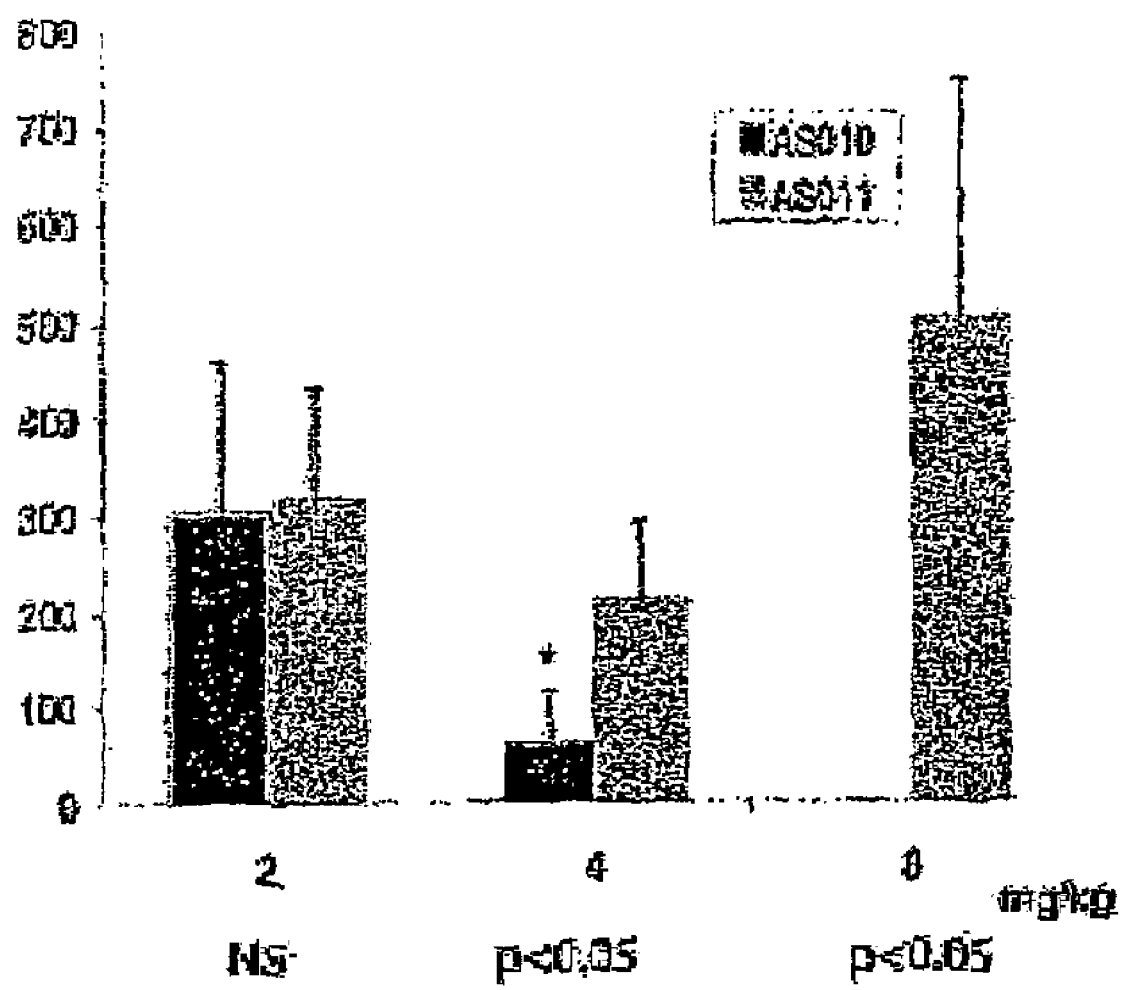
FIG. 15 depicts the decrease in tumour weight following treatment of in vivo xenografts of the human colorectal carcinoma cell line HCT116 in nude mice with antisense oligonucleotide A10. Stars above the bars indicate statistical significance (two-sided student t-test).

Antisense oligonucleotide A10 also reduced tumour growth of HCT116 colon cancer cells in nude mice (FIG. 14B-*experimental* as described above for A549 cells). HCT116 cells appeared to be extremely sensitive to reductions in MBD2 as indicated by the complete regression of tumours in some mice at each dose concentration (FIG. 14D). Maximal effect on HCT116 was achieved at a dose of 8 mg/kg. Numbers of tumour-free mice for 2, 4, and 8 mg/kg groups were 5/8, 7/8, 8/8 for A10, and 1/8, 1/6 and 1/8 for A11 treatments. Two mice in the A11 4 mg/kg group died of cachexia, perhaps due to tumour burden. None of the antisense treated mice implanted with HCT116 cells died before sacrifice. A dose dependent reduction in tumour mass with A10 antisense treatment was observed when the tumour mass was determined following sacrifice of the animals (FIGS. 15 and 13B).

Example 7

In Vivo Toxicity Testing

The absence of specific toxic effects on proliferating tissues in vivo was determined for antisense oligonucleotide A10. For the experiment conducted in Example 5, animal weight was monitored throughout the experiment. The results shown in FIG. 12 demonstrate that the antisense oligonucleotide had no effect on animal weight at any of the concentrations used in this experiment.

Blood samples were obtained at sacrifice from the treated mice in Example 6 and screened for various markers of in vivo toxicity (Table 3). Throughout the various dosing concentrations, no differences were seen between A10 and A11 for hematological measurements, indicating that the blood cell precursors which are often sensitive to chemotherapeutic regimens were largely unaffected by serial dosing of the antisense oligonucleotide. Platelet numbers were, however, increased above normal levels, regardless of treatment or dose; this is probably caused by the multiple tail vein injections. Urea, creatinine, aspartate aminotransferase (AST) and alanine aminotransferase (ALT), indices of liver, muscle, and kidney damage, similarly showed no negative effects from in vivo treatment. Swelling of the inguinal lymph nodes was a nonspecific but dose-dependent effect of the oligonucleotides that occurred in several mice treated with doses of 4 or 8 mg/kg.

Analysis of hematological values and serum biochemical parameters was performed by McGill University Animal Resources centre Diagnostic and research support service using standard procedures.

TABLE 3

| | In vivo Toxicity Testing for Antisense Oligonucleotide A10 | | | | | |
|---|---|---|---|---|---|---|
| | 2 mg/kg | | 4 mg/kg | | 8 mg/kg | |
| | A10 | A11 | A10 | A11 | A10 | A11 |
| Hematocrit | 0.44 ± 0.01 | 0.45 ± 0.01 | 0.46 ± 0.01 | 0.44 ± 0.01 | 0.44 ± 0.01 | 0.45 ± 0.01 |
| Hemoglobin (g/l) | 152.88 ± 4.3 | 154.75 ± 3.3 | 156.81 ± 3.2 | 149.46 ± 2.0 | 153.02 ± 1.6 | 154.81 ± 3.1 |
| RBC ($10^{12}$)/l | 9.07 ± 0.2 | 9.11 ± 0.3 | 9.32 ± 0.2 | 8.78 ± 0.2 | 9.14 ± 0.1 | 9.43 ± 0.3 |
| MCV (fl) | 48.88 ± 0.5 | 49.56 ± 0.4 | 49.44 ± 0.6 | 49.69 ± 0.3 | 48.41 ± 0.3 | 48.19 ± 0.4 |
| MCH (pg) | 16.85 ± 0.2 | 17.02 ± 0.2 | 16.87 ± 0.2 | 17.06 ± 0.2 | 16.83 ± 0.2 | 16.47 ± 0.3 |
| MCHC g/l | 345.19 ± 3.2 | 345.32 ± 3.4 | 341.13 ± 2.4 | 344.23 ± 3.7 | 348.35 ± 2.2 | 343.22 ± 5.0 |
| WBC ($10^9$/l) | 7.19 ± 0.6 | 6.04 ± 0.7 | 8.23 ± 0.5 | 6.28 ± 1.0 | 8.04 ± 0.7 | 9.23 ± 0.7 |
| Platelets ($10^9$/l) | 821.00 ± 119.5 | 662.13 ± 81.3 | 630.81 ± 89.6 | 796.79 ± 84.0 | 608.54 ± 86.9 | 591.90 ± 64.7 |
| Urea (mM) | 7.8 ± 0.5 | 7.7 ± 0.2 | 8.9 ± 1.1 | 7.6 ± 0.6 | 8.0 ± 0.6 | 9.1 ± 0.7 |
| Creatinine (mM) | 39.4 ± 1.2 | 40.8 ± 0.8 | 40.5 ± 1.3 | 41.0 ± 1.2 | 40.3 ± 1.4 | 38.5 ± 1.5 |
| Albumin (g/l) | 37.9 ± 0.4 | 38.2 ± 0.4 | 37.5 ± 0.5 | 38.1 ± 0.8 | 37.6 ± 0.8 | 36.4 ± 0.6 |
| ALT (U/l) | 82.1 ± 19.9 | 83.2 ± 18.0 | 113.6 ± 33.5 | 79.7 ± 19.1 | 92.1 ± 27.2 | 93.9 ± 24.0 |
| AST (U/l) | 216.3 ± 31.8 | 165.1 ± 25.3 | 256.3 ± 79.4 | 237.8 ± 72.2 | 297.1 ± 90.7 | 282.6 ± 60.5 |

RBC—red blood cells,

WBC—white blood cells,

AST—aspartate aminotransferase and

ALT—alanine aminotransferase.

Errors are SEM for 14-16 mice per group.

Example 8

In Vitro Assay for Demethylase Activity

The assay is based on the fact that in vitro methylation of vector CMV-GFP followed by transfection into HEK cells treated with the histone deacetylase inhibitor trichostatin A, results in demethylation of the vector DNA by endogenous demethylase [Cervoni, N. & Szyf, M., (2001) *J. Biol. Chem.*, 276:40778-40787]. The methylated form of CMV-GFP is not expressed by the cells, whereas the demethylated form is expressed and the GFP protein is readily detected by live fluorescence microscopy.

HEK cells treated with trichostatin A and transfected with vector CMV-GFP are grown in 96 well plates and are treated with oligonucleotide inhibitors of MBD2/dMTase. 96 hours after initiation of treatment, the level of inhibition is determined by counting fluorescence-expressing cells by microscopy as previously described. The assay can be conducted rapidly by reading the fluorescence of the expressed GFP using a fluorometer with a 96 well plate reader.

Example 9

Differential Expression Analysis of Cells Treated with MBD2/dMTase Oligonucleotide Inhibitors Using Gene Arrays Affymetrix huGene F1™ arrays (Affymetrix, Santa Clara, Calif.) are used for expression profiling. RNA is prepared from cells treated with MBD2/dMTase oligonucleotide inhibitors and from control cells as described above. cDNA is synthesised from the isolated poly(A)+ mRNA using SuperScript Choice kit (GEBCO/BRL). cRNA is prepared in an in vitro transcription reaction in the presence of biotin-11-CTP and biotin-16-CTP using T7 polymerase (Megascript kit, Ambion). Arrays are hybridised with the biotinylated in vitro transcription products for 16 hours at 45° C. using the manufacturer's hybridization buffer. A two-step protocol is used to detect hybridization intensity, consisting of primary incubation of arrays with a streptavidin-phycoerythrin conjugate followed by a labeling step with a goat anti-streptavidin antibody (Vector). The array chips are then scanned and the digitised image data is processed with the GeneChip™ software (Affymetrix) to identify genes that are up- or downregulated in response to treatment with the oligonucleotide inhibitors.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. An oligonucleotide inhibitor chosen from an antisense oligonucleotide or an analogue thereof, consisting of the nucleotide sequence as set forth in SEQ ID NO:12, wherein said oligonucleotide inhibitor inhibits expression of a mammalian MBD2/demethylase gene.

2. The oligonucleotide inhibitor according to claim 1, wherein said oligonucleotide inhibitor comprises one or more phosphorothioate backbone linkages.

3. The oligonucleotide inhibitor according to claim 1, wherein said oligonucleotide inhibitor comprises one or more 2'-O-methyl modified bases.

4. An expression vector comprising an insert sequence, wherein said insert sequence consists of a sequence encoding the oligonucleotide inhibitor as set forth in SEQ ID NO:12.

5. An isolated host cell transformed or transfected with the oligonucleotide according to claim 1.

6. A pharmaceutical composition comprising the oligonucleotide inhibitor according to claim 1, in association with a pharmaceutically acceptable carrier for the manufacture of a medicament.

7. A method for inhibiting expression of a mammalian MBD2/demethylase gene in a mammal comprising administering to said mammal a therapeutically effective amount of an oligonucleotide inhibitor chosen from an antisense oligonucleotide, or an analogue thereof, consisting of the nucleotide sequence as set forth in SEQ ID NO:12, wherein said oligonucleotide inhibitor inhibits expression of a mammalian MBD2/demethylase gene.

8. The method according to claim 7, wherein said mammal is a human.

9. A method for treating lung cancer and/or colorectal cancer in a mammal comprising administering to said mammal a therapeutically effective amount of an oligonucleotide inhibitor chosen from an antisense oligonucleotide, or an analogue thereof, consisting of the nucleotide sequence as set forth in SEQ ID NO:12, wherein said oligonucleotide inhibitor inhibits expression of a mammalian MBD2/demethylase gene.

10. The method according to claim 9, wherein said oligonucleotide inhibitor inhibits lung and/or colorectal cancer cell growth.

11. The method according to claim 9, wherein said oligonucleotide inhibitor inhibits lung and/or colorectal cancer cell proliferation.

12. The method according to claim 9, wherein said mammal is a human.

* * * * *